United States Patent
Adler et al.

(10) Patent No.: US 7,171,038 B2
(45) Date of Patent: Jan. 30, 2007

(54) METHOD AND APPARATUS FOR INSPECTING A SUBSTRATE

(75) Inventors: David Adler, San Jose, CA (US); Kirk Bertsche, San Jose, CA (US); Mark McCord, Mountain View, CA (US); Stuart Friedman, Palo Alto, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 797 days.

(21) Appl. No.: 10/017,860

(22) Filed: Dec. 14, 2001

(65) Prior Publication Data

US 2002/0161534 A1 Oct. 31, 2002

Related U.S. Application Data

(60) Provisional application No. 60/256,168, filed on Dec. 15, 2000.

(51) Int. Cl.
G06K 9/00 (2006.01)
(52) U.S. Cl. ........................ 382/149; 250/307
(58) Field of Classification Search ........... 382/144, 382/145, 147, 149; 29/833; 438/16; 348/126; 250/306, 307, 310, 311, 397, 399; 356/390, 356/394, 237.1, 237.2, 237.4, 237.5
See application file for complete search history.

(56) References Cited

U.S. PATENT DOCUMENTS

| | | | |
|---|---|---|---|
| 4,912,313 A | 3/1990 | Kato et al. | |
| 4,926,487 A | 5/1990 | Yoshida et al. | |
| 5,097,127 A | 3/1992 | Hildenbrand et al. | |
| 5,502,306 A | 3/1996 | Meisburger et al. | |
| 5,557,105 A | 9/1996 | Honjo et al. | |
| 5,644,132 A | 7/1997 | Litman et al. | |
| 5,659,172 A * | 8/1997 | Wagner et al. | 250/307 |
| 5,717,204 A | 2/1998 | Meisburger et al. | |
| 5,822,055 A * | 10/1998 | Tsai et al. | 356/237.1 |
| 5,825,482 A | 10/1998 | Nikoonahad et al. | |
| 5,917,588 A * | 6/1999 | Addiego | 356/237.2 |
| 5,973,323 A | 10/1999 | Adler et al. | |
| 6,021,214 A | 2/2000 | Evans et al. | |
| 6,081,325 A | 6/2000 | Leslie et al. | |
| 6,087,659 A | 7/2000 | Adler et al. | |
| 6,141,038 A | 10/2000 | Young et al. | |
| 6,169,282 B1 * | 1/2001 | Maeda et al. | 250/310 |
| 6,172,363 B1 * | 1/2001 | Shinada et al. | 250/310 |
| 6,200,823 B1 | 3/2001 | Steffan et al. | |
| 6,252,981 B1 | 6/2001 | Guest et al. | |
| 6,272,236 B1 | 8/2001 | Pierrat et al. | |
| 6,288,782 B1 | 9/2001 | Worster et al. | |
| 6,348,690 B1 | 2/2002 | Iwabuchi et al. | |
| 6,661,912 B1 * | 12/2003 | Taguchi et al. | 382/145 |

FOREIGN PATENT DOCUMENTS

WO    WO 01/88514 A1    11/2001

\* cited by examiner

*Primary Examiner*—Samir Ahmed
(74) *Attorney, Agent, or Firm*—Okamoto & Benedicto LLP

(57) ABSTRACT

A method and apparatus for inspection and review of defects is disclosed wherein data gathering is improved. In one embodiment, multiple or segmented detectors are used in a particle beam system.

5 Claims, 26 Drawing Sheets

METHOD AND APPARATUS FOR INSPECTING A SUBSTRATE

CROSS REFERENCE TO RELATED APPLICATION

This application claims priority to U.S. Provisional Patent Application Ser. No. 60/256,168, filed Dec. 15, 2000, the disclosure of which is hereby incorporated by reference.

BACKGROUND OF THE INVENTION

To achieve high manufacturing yields, the semiconductor industry depends on careful inspections of photomasks, bare silicon wafers, and processed silicon wafers. The inspection requirements are becoming more stringent as the industry inscribes smaller features on each new generation of integrated circuits. The resolution of optical inspection systems is becoming inadequate to find the small defects which can spoil the performance of an integrated circuit. To find smaller defects, the industry will increasingly rely on electron-beam inspection systems and review stations, which offer at least 10 times better resolution than optical systems. These inspection systems are variations on the traditional scanning electron microscope. Such inspection systems and review stations may, of course, find use in evaluation of other samples, such as biological samples, metallurgical samples, and the like.

Scanning Electron Microscopes

In a scanning electron microscope (SEM), a beam of electrons perhaps 3.5 nanometers in diameter scans across the surface of a substrate (for example, a photomask, a bare silicon wafer, a processed silicon wafer, or another sample). The electrons in the beam, known as "primary electrons," penetrate the substrate and dislodge electrons within the material. Some of these dislodged electrons, known as "backscattered electrons" or "secondary electrons," escape from the surface of the substrate.

A detector captures the emitted electrons. The SEM's electronic imaging system can transform the detector's output into a black-and-white image of the surface. Darker areas of the image correspond to areas on the substrate which emitted fewer electrons, and lighter areas of the image correspond to areas of the substrate which emitted more electrons.

SEM-Based Inspection Systems

When an SEM-based inspection system acquires an image of a region on a wafer or a photomask, it has no immediate way to know whether the pattern in that region is correct. To find defects, the system typically captures not only an image of the region to be inspected (the "test image") but also a reference image, then compare the two with high-speed electronics. In "die-to-die" mode, the reference image is a corresponding area on a nominally identical die on the same wafer or photomask. In "array mode," the reference image is a nominally identical pattern in a different location on the same die, for example, on DRAM chips or on photomasks for exposing DRAM chips.

The system electronically aligns the test image with the reference image, than compares them to look for significant differences. Most systems execute the comparison by assigning a numerical gray scale value (from, say, 0 to 256) to each pixel, then subtracting the gray scale values of the corresponding pixels in the two images. They can calculate and display a "difference map" or "defect map" in which the gray scale value of each pixel is the difference between its value in the test image and its value in the reference image. Defects can appear as bright areas in the difference map.

The Defect Threshold

One might expect that the difference in gray scale value would be zero for most of the pixel pairs if the sample contains few real defects. However, slight differences in gray scale values between corresponding pixels in the test and reference images occur frequently due to various sources of system noise and to processing-induced pattern variations which might be too subtle to impair circuit performance.

The designer and/or the operator of the inspection system have to define a "defect threshold," i.e., a difference in gray scale values. If corresponding pixels in the test and reference images differ in gray scale value by an amount less than the threshold, the system will ignore them. If they differ by an amount equal to or greater than the threshold, the system will report a defect. In that case, the system may also scan a third nominally identical region, an "arbitrator" to determine whether the defect lies in the test image or in the reference image. The system concludes that the image which matches the arbitrator is correct and the one which differs contains the defect.

The selection of a defect threshold involves a complex and serious engineering tradeoff between sensitivity and false or nuisance defects. If the defect threshold is set very low, the system will be more sensitive; it will almost certainly find all the significant defects which could impair circuit performance. However, it may find thousands of "false defects," areas in which the patterns are actually identical, but the gray scale values differ because of system noise. It may also find thousands of "nuisance defects," areas in which the patterns differ but the differences are small enough to ignore. The operator may have to review thousands of defect reports to cull the real defects from the false and nuisance defects.

If, on the other hand, the defect threshold is set very high, the system will report few false defects and few nuisance defects. However, it will be less sensitive, and it might miss a critical defect which can ruin the circuit.

The Effect of Detector Position

In early generations of SEM's, a single detector, often referred to as a "total-yield detector," captured virtually all the backscattered and secondary electrons, no matter what their initial trajectory, with help from electrical or magnetic fields. Since the rate of secondary electron emission depends sensitively on the materials and on the topography, these instruments could produce high-resolution images of, for example, metal lines on an oxide or quartz surface. A printed image would easily reveal defects such as an extra metal line, a missing metal line, a broken metal line, etc.

However, instruments with a single total-yield detector are less successful at revealing variations in surface topography; i.e., at finding areas which rise above or dip below the plane of the surface. For example, during chemical-mechanical polishing of a silicon wafer, a dust particle or an impurity in the slurry can create a "microscratch," an indentation which might be 0.1 micron wide by 0.1 micron deep by 1 micron long. A microscratch can be a critical defect in an integrated circuit because metal can fill it, creating an electrical short between two lines that are supposed to be isolated. A total-yield detector can't detect the microscratch on the basis of materials contrast because the microscratch is just a tiny gouge within one material.

To detect microscratches and other small variations in surface topography, we can get them to cast "shadows" in an SEM image by using a detector which selectively collects secondary electrons moving toward one side or the other. This "shadowing" will occur in any system which does not produce a point-to-point image of the sample on the detector, i.e. electrons emitted from the same point but at different angles from the sample will arrive at different positions on the detector. For example, the instrument might contain a detector positioned to the side of the substrate just above the plane of the substrate surface, and strategically placed electric or magnetic fields might direct only the electrons moving toward that side into the detector. The resultant shadows make it easier to see microscratches and other variations in surface topography.

A detector in a scanning electron-beam will find certain defect types with greater or lesser sensitivity, depending on its elevational angle. Mounted overhead, it will be more sensitive to differences in materials; mounted to the side, it will be more sensitive to microscratches and other variations in surface topography. To optimize sensitivity for many defect types, some SEM inspection systems rely on two detectors: one mounted overhead, one mounted to the side.

Prior Art SEM-Based Inspection Systems with Two Detectors

The presence of two or more detectors raises the question of how to apply the information which a plurality of detectors provides. One prior art method uses the signal from the second detector to provide a "cross-check" for the signal from the first detector.

In this prior art method, each of two detectors in the inspection system looks at secondary electrons from two nominally identical regions. For clarity, we refer to the two detectors as Detector A (mounted on top) and Detector B (mounted on the side) and assume it's a die-to-die inspection of a processed silicon wafer.

Detector A takes an image of a specific region on a die (the test image) and an image of a nominally identical region on an adjacent die (the reference image). For each pair of corresponding pixels, the system subtracts the gray scale values and compares the difference with the threshold. If the difference is below the threshold, the system ignores them. If the difference equals or exceeds the threshold, the system reports a defect. The one-dimensional plot in FIG. 1a illustrates this part of the method.

Detector B repeats the process: it takes an image of the same two regions imaged by Detector A. For each pair of corresponding pixels, the system reports a defect only if the difference in gray scale values exceeds the threshold value. The one-dimensional plot in FIG. 1b illustrates this part of the method.

One significant weakness of the method disclosed by the prior art is that it attempts to distinguish real defects from false or nuisance defects on the basis of data from a single detector. It identifies defects first on the basis of two sets of image data taken by Detector A, then on the basis of two sets of image data taken by Detector B. It describes a data processing technique that essentially uses the two one-dimensional plots shown in FIG. 1. This prior art method doesn't acknowledge or recognize any advantage to be gained from combining more than two data sets in innovative ways before defining a defect. As a result, the prior art doesn't ameliorate the difficult tradeoff between sensitivity and false defects. Furthermore, it lends the operator very little flexibility in terms of his ability to look selectively for certain defect types.

In another prior art method, signals from a backscattered electron detector and a secondary electron detector are compared to produce information concerning the location, size and shape of features on a substrate. This prior art method makes use the unique characteristics of the secondary and backscattered electron waveforms to provide additional information concerning the surface under inspection.

In yet another prior art method, signals from two different detectors are combined to produce a composite image of a high aspect ratio structure. The detectors may be separately optimized for imaging the top and bottom, respectively, of the high aspect ratio structures. The resulting image may have an extended focus.

Plural detectors have also been used in the prior art to produce composite images in which differences in electron trajectory or position are represented in a color display. The positions of such detectors have been varied about the specimen, and differences between the signals from these detectors have been analyzed in such systems.

None of the aforementioned prior art methods takes full advantage of the capabilities of a multi-detector SEM to inspect substrates.

SUMMARY OF THE INVENTION

This invention involves novel methods and apparatus for combining the information from two or more detectors in an inspection system, review station, CD SEM, or the like with a scanning electron beam.

One object of the present invention is to allow an SEM-based inspection system to address more successfully the tradeoff between sensitivity and false or nuisance defects. Several of the inventions described here will allow the inspection system to find virtually all the defects that matter while presenting the operator with a minimum of false and nuisance defects to review.

Another object of the present invention is to provide methods by which an operator can selectively review specific types of defects.

The methods and apparatus disclosed here will allow an automated inspection system to inspect a substrate to find defects, to redetect defects already found by another inspection system (such as a lower-resolution optical inspection system), and to classify defects according to their type. These inventions will allow the system to operate in array mode, die-to-die mode, or die-to-database mode. They will be consistent with inspection systems that have either a moving stage or a stationary stage. The methods include ways of processing both digital and analog image data.

Most of these inventions are based on the key insight that it is useful to combine, process, and analyze data sets from two or more detectors before deciding whether a given anomaly is a significant defect.

More broadly, the object of this invention is to provide an automated method by which a electron-beam inspection system can find or redetect defects and classify those defects according to various attributes (e.g., size, shape, material, and context). In practice, the inspection system would be able to analyze the types of defects found and infer which parts of a wafer process line were causing the defects. It would also store this information in a file which someone could examine later.

DETAILED DESCRIPTION OF TH PREFERRED EMBODIMENTS

The following examples illustrate a variety of preferred methods and apparatus for for inspecting, redetecting, and/or classifying defects with an inspection system that exposes substrates to charged particles, detects the charged particles emitted from or scattered by the substrates, and processes the data.

Figure 1:
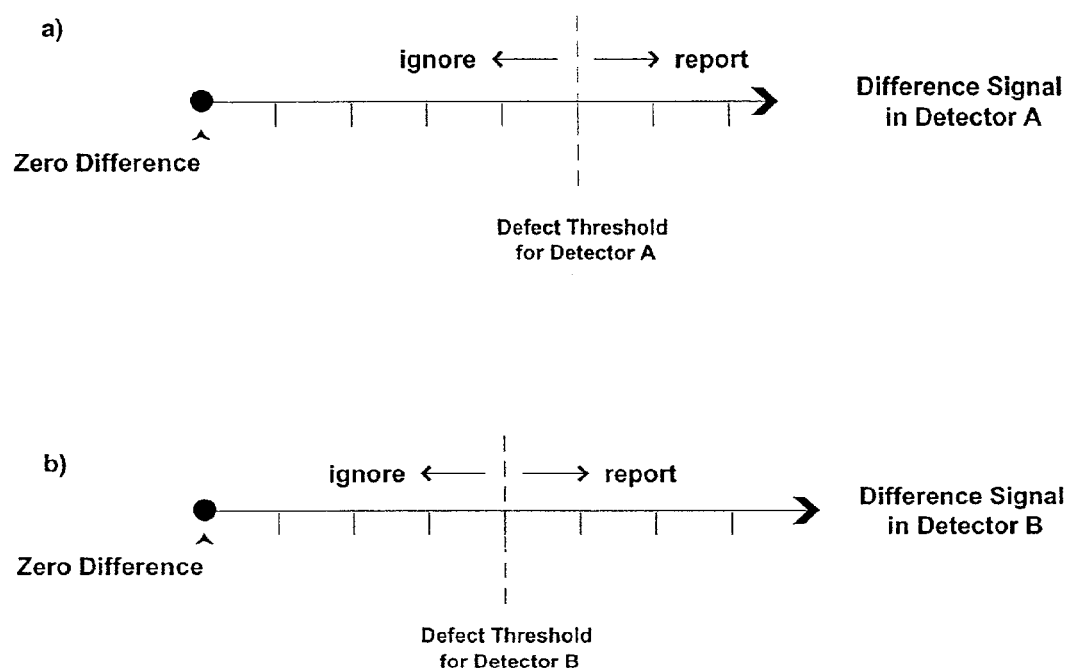
FIG. 1 symbolically illustrates a method of detecting defects in the prior art.
Figure 2:
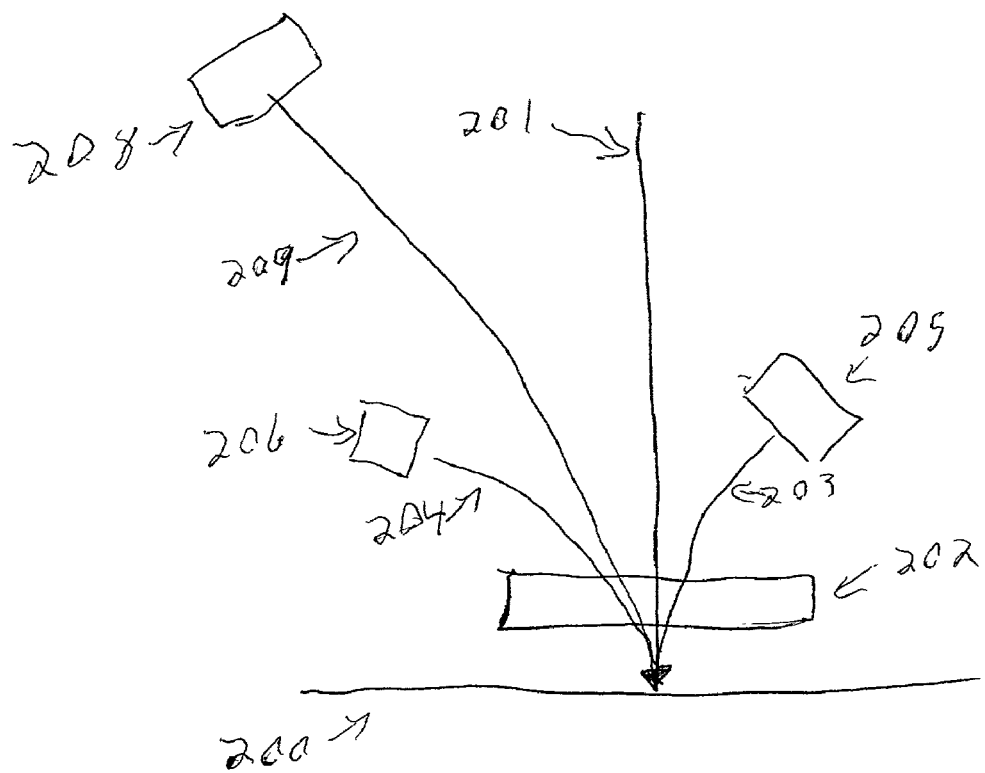
FIG. 2 illustrates one possible hardware configuration.

FIG. 2 illustrates an apparatus of an embodiment of the invention including a plurality of detectors. In this apparatus, electrons from incident beam 201 impinge upon substrate 200 and cause secondary and/or backscattered electrons 203 and 204 to be emitted from the substrate. Detectors 205 and 206 are used to detect electrons 203 and 204. Detectors 205 and 206 may be positioned so that one detects primarily secondary electrons, while the other detects primarily backscattered electrons. Alternatively, both detectors may detect secondary electrons, or both detectors may detect backscattered electrons. Selection of secondary electrons or backscattered electrons may be made by use of an energy filter on or before the detector. Detectors 205 and 206 are positioned at an azimuthal angle relative to one another that preferably ranges between 90 degrees and 180 degrees.

Detectors 205 and 206 may be positioned above an objective lens 202, as shown, or could instead be positioned below the objective lens so that the electrons 204 and 203 reach the detectors 205 and 206 without passing through objective 202. In addition, an electron separator 207 (which could be, e.g., a Wein filter or magnetic prism) may be used to alter the trajectory of secondary or backscattered electrons 209 returning up the column and direct those electrons to detector 208.

Signals derived from any or all of detectors 205, 206 and 208 may be used separately or in combinations, as described elsewhere herein, to inspect or review substrate 201. Furthermore, detector 208 and/or any of the other detectors used may be a single detector, multiple detectors, or a position sensitive detector. Position sensitive detectors, such as segmented detectors, and possible methods of their use are described in more detail hereinafter.

Die-to-Die Inspection

Figure 3:
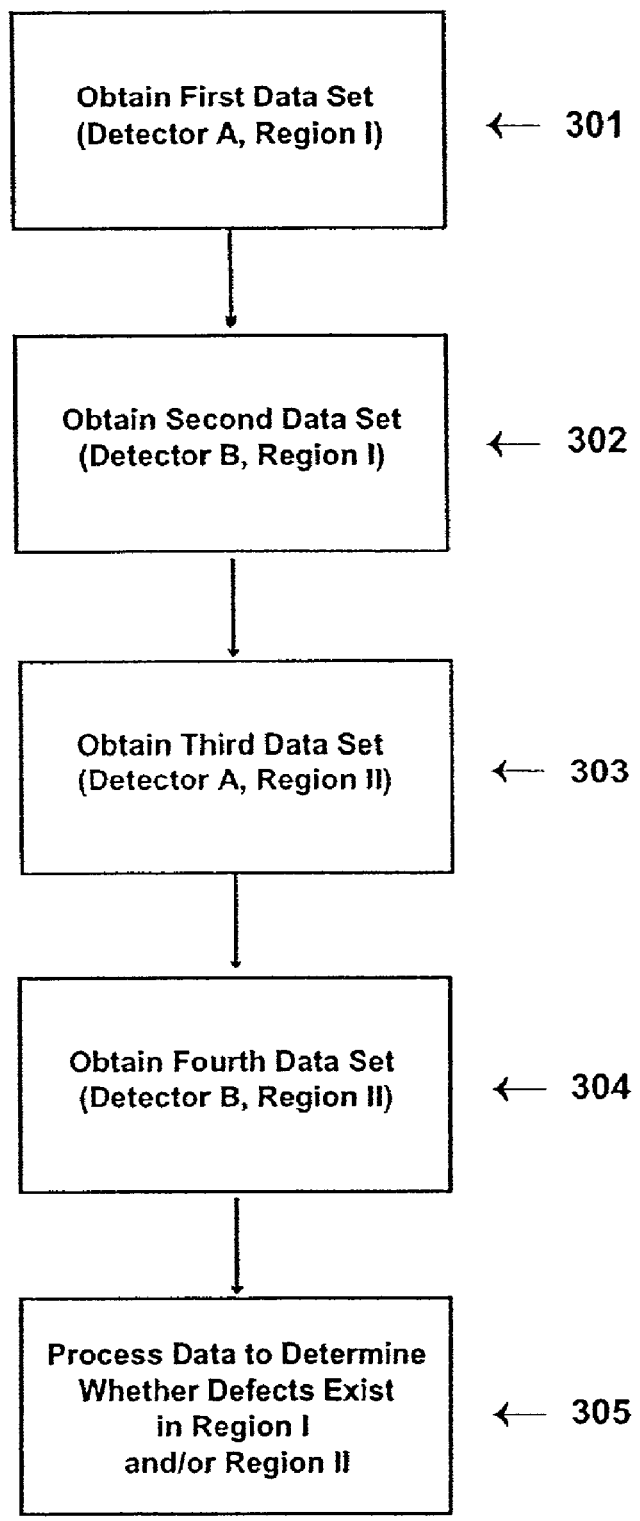
FIG. 3 illustrates a novel method for die-to-die inspection.

FIG. 3 illustrates a novel method of inspecting and/or characterizing a substrate in die-to-die mode. In this method, an inspection system exposes a substrate to either a flood or focused beam of electrons or other charged particles. The system then detects secondary electrons from that substrate with at least two detectors. The detectors collect image data from two nominally identical die (Region I and Region II) on the same substrate. The method encompasses the following five steps:

Detector A obtains a set of image data from Region I (301),

Detector B obtains a set of image data from Region I (at least a portion of it) (302), Detector A obtains a set of image data from Region II (303), Detector B obtains a set of image data from Region II (at least a portion of it) (304), and the inspection system processes the data from all four data sets to determine whether a defect exists in either Region I or Region II (305).

The system can complete steps 301 through 304 in any sequence. In most cases, it will be more efficient to complete steps 301 and 302 simultaneously and steps 303 and 304 simultaneously.

The novelty of this method lies in step 305, processing the data from all four data sets to determine whether a defect exists in either Region I or Region II. Generally, a first step in processing the image data from multiple data sets is aligning the images to each other.

This method described by steps 301 through 305 is useful for inspecting a substrate anew, for redetecting a defect already found by another inspection system (such as an optical inspection system, which has lower resolution than an electron-beam system), or for classifying defects into different types. In this method, the substrate could be a semiconductor wafer, a singulated die, a package substrate, a reticle, or a photomask. The detectors can be line array sensors, individual detectors, two-dimensional array sensors, time delay integration sensors, or combinations thereof.

In one embodiment, two or more individual sensors are positioned to obtain the angular distribution of the electrons. Alternatively, one or more segmented detectors are used to determine the distribution. In either case, the some or all of the detectors may have energy filters to determine the energy and/or energy spread of the electrons.

In one embodiment of the invention, the substrate being inspected is a phase shift mask or other mask having topographic structures of interest. By using a plurality of detectors, the topography of the reticle may be better inspected, and a topographic comparison can be made in die:die mode, die:database mode, or by any other suitable method. In die to database mode, the rendered database could be produced such that height information concerning the features of the reticle is produced. This will permit a three dimensional comparison to the actual reticle or photomask. Such three dimensional comparison could be done using the multi detector SEM system described herein, or by any other suitable technique that provides height information.

Processing the Data

We now describe one method of executing step 305 above, processing the data from all four data sets simultaneously. The method, illustrated in FIG. 4, encompasses four steps:

- calculate the difference signal for each pixel with Detector A (401),
- calculate the difference signal for each pixel with Detector B (402),
- perform a mathematical operation on the two difference signals (403), and
- compare the result of this operation with a difference threshold (404).

In step 401, the term "difference signal" means the difference in gray scale values between a pixel in Region I and the corresponding pixel in Region II, as measured by Detector A.

In step 402, the term "difference signal" means the difference in gray scale values between a pixel in Region I and the corresponding pixel in Region II, as measured by Detector B.

Figure 5:
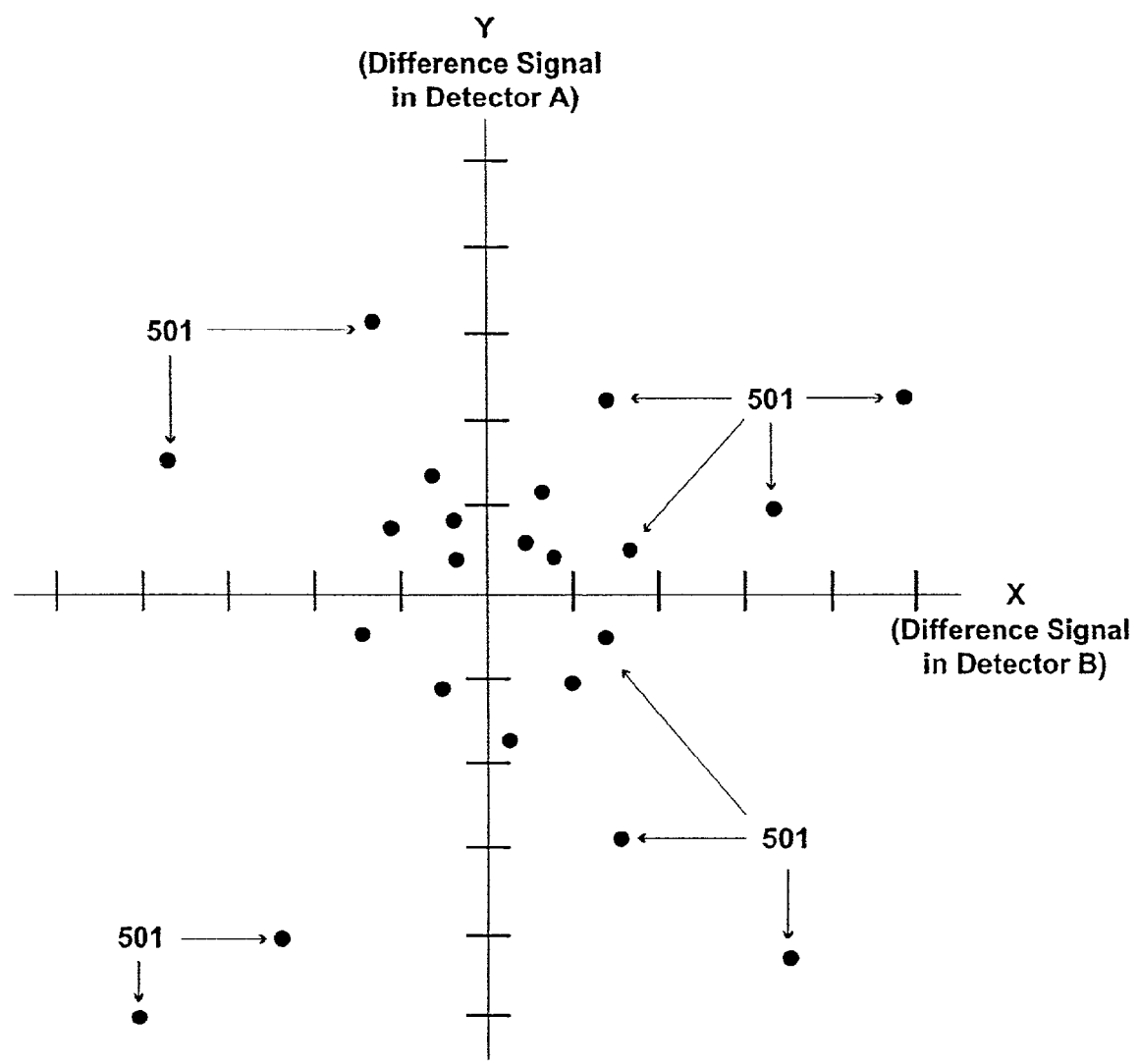
FIG. 5 illustrates a two-dimensional scatter plot in which the Y-axis is the difference from Detector A and the X-axis is the difference signal from Detector B. Each data point represents data for a "pixel pair;"
Figure 6:
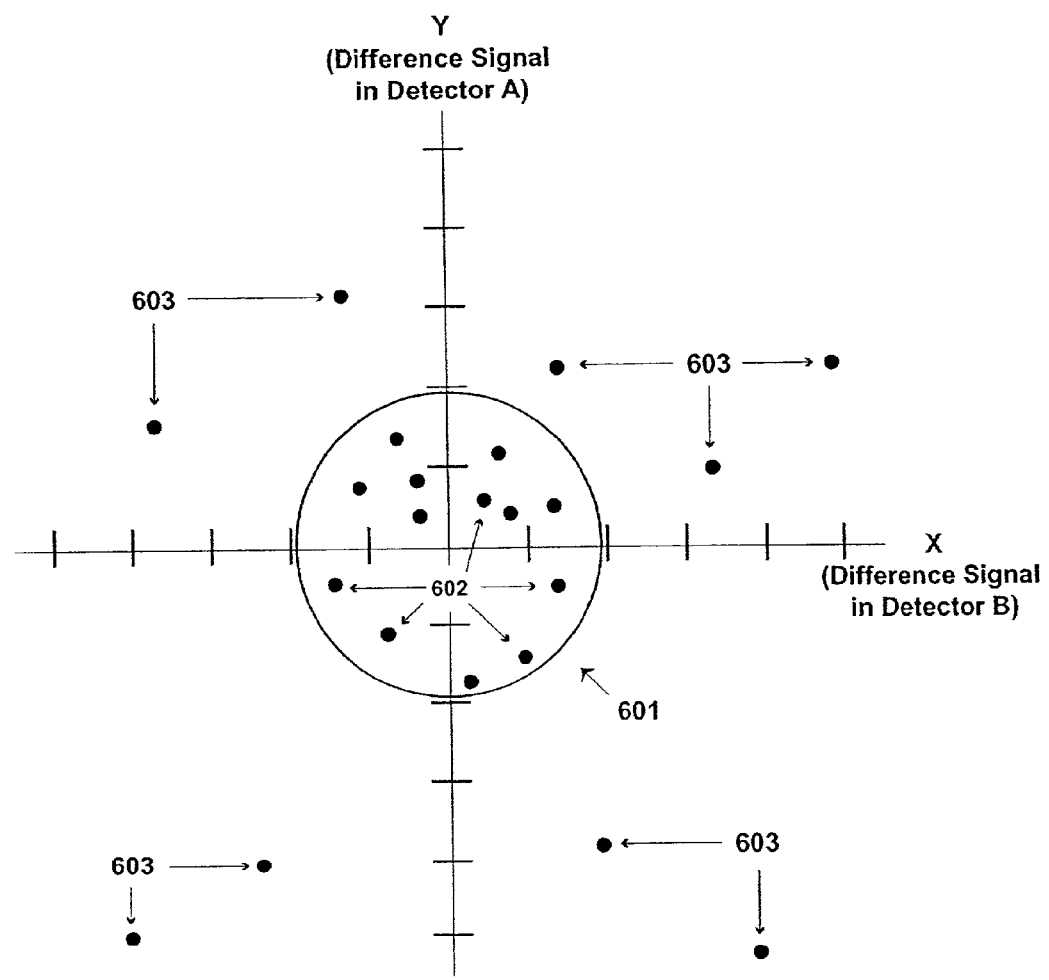
FIG. 6 illustrates a defect threshold.
Figure 7:
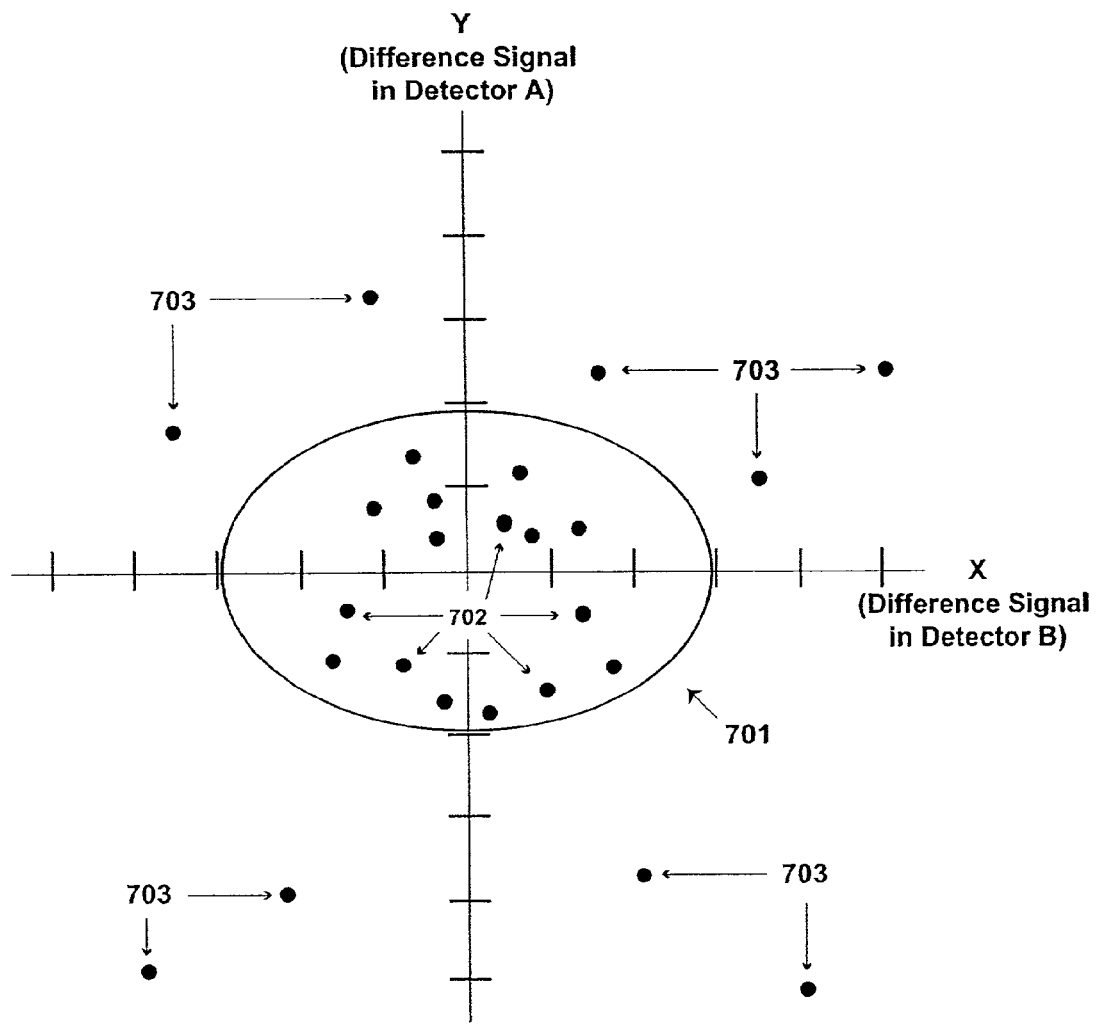
FIG. 7 illustrates an elliptical defect threshold.

In step 403, the mathematical operation might be, for example, to square the two difference signals, add the two squares, and take the square root of the sum. FIGS. 5, 6, and 7, taken together, will clarify the logic for this step. However, such a mathematical operation is merely one example of many possible methods of processing the data in accordance with the present invention. For example, one may use a generalized equation of the form:

$$A = (P(BD_{A1} + CD_{B1})^M / (SD_{A1} + TD_{B1})^Q + (ED_{A2} + FD_{B2})^N / (UD_{A2} + VD_{B2})^R)^K;$$

where the values of B, C, E, F, M, K, P, Q, R, S, T, U, V and N represent constants and/or functions of other variables. These values may be predetermined from theory and/or may be determined empirically. They may be optimized automatically by the operator or an Automated Defect Classification (ADC) program. Such a program may optimize the aforementioned values in these or other such equations during setup of such an ADC program. Still other methods of processing the data are possible, such as forming a composite, three-dimensional image of each Region using the combined outputs of the detectors. These resulting composite images can then be compared with one another or otherwise processed in accordance with the invention.

FIG. 5 shows a two-dimensional scatter plot in which the Y-axis is the difference signal from Detector A and the X-axis is the difference signal from Detector B. Each data point 501 represents coordinates for a "pixel pair" We define a "pixel pair" as two corresponding pixels or adjacent groups of pixels in analogous locations in Region I and Region II. Since the regions are nominally identical, the two pixels are nominally identical and therefore would always give a difference signal of zero in an ideal situation, i.e., if the system were free of noise and the two die were free of even the slightest defects. Of course, the pixel locations need not correspond exactly, and for example, adjacent pixels may be substituted for one another, or data from groups of nearby pixels may be averaged, differentiated, filtered to select maximum of minimum values, smoothed, or otherwise processed prior to taking a difference signal. Moreover, a technique known as segmentation and thresholding may be employed in which each image is divided (segmented) into regions according to the relative intensity, contrast, etc of the pixels therein, and the image is then thresholded to reduce noise within each segment. Information derived from different detectors may be combined in the segmentation and/or thresholding processes to improve the result.

For each data point 501 in FIG. 5, the Y-axis value is the difference signal given by Detector A and the X-axis value is the difference signal given by Detector B for that pixel pair. Each data point 501 in FIG. 5 therefore reflects a composite difference signal which takes into both the difference signal from Detector A and the difference signal from Detector B. At this point, the system has processed data from all four detectors, and it has not yet determined which of these data points constitute defects.

Figure 4:
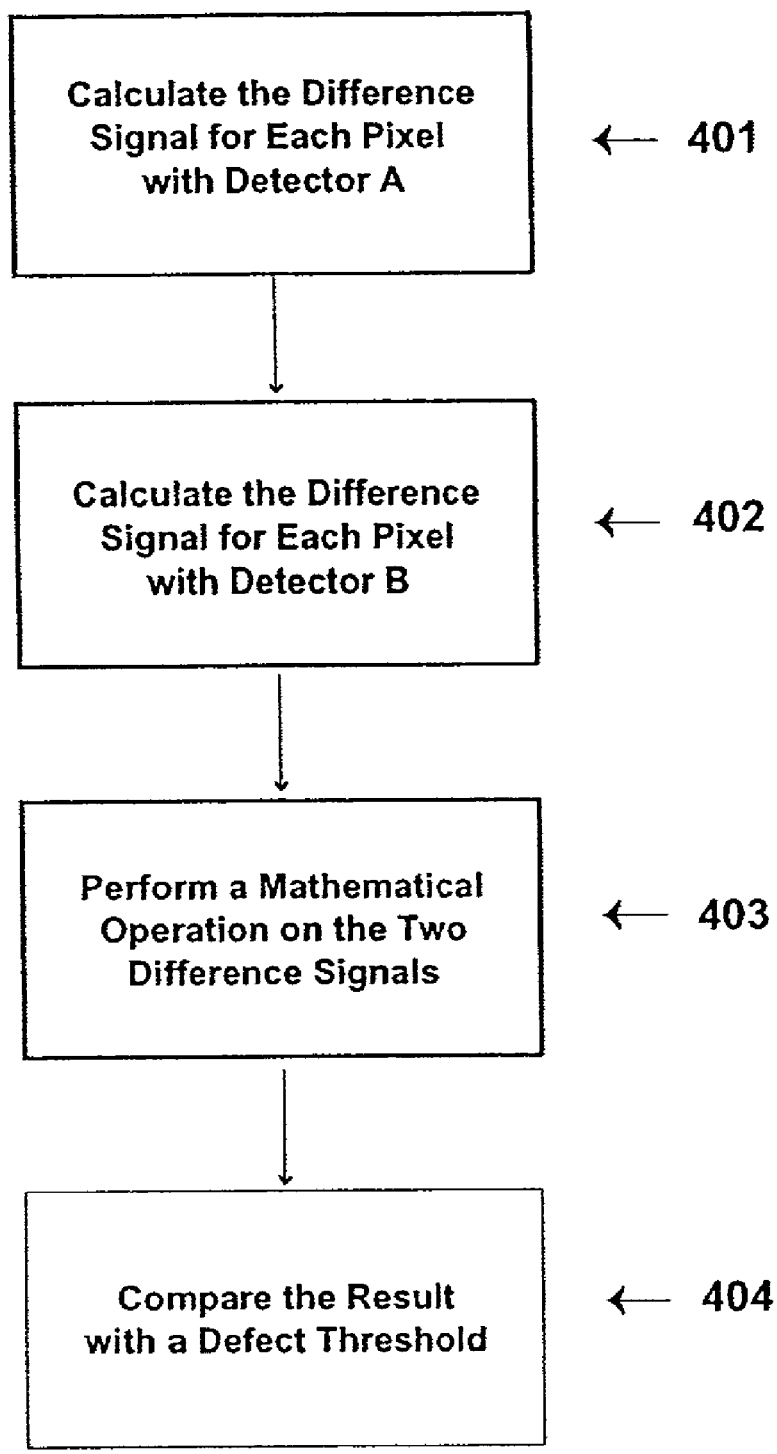
FIG. 4 illustrates a novel method of processing data from four data sets.

In step 404 of FIG. 4, we compare that collective difference signal with a defect threshold, as illustrated in FIG. 6, where the defect threshold or decision boundary is a circle 601 with its center at the origin. The system would ignore the data points 602 inside the circle 601 and report the data points 603 outside the circle as defects. In practice, the system operator would choose the defect threshold 601 (the radius of the circle) to gain whatever sensitivity is necessary to capture all real defects 603 while keeping the rates of false defects and nuisance defects 602 at a tolerable level.

Tables 1 and 2 illustrate some of the advantages of using a composite difference signal. Both tables are matrices in which the column headings are the difference signal from Detector A and the row headings are the difference signals from Detector B. They illustrate the ways in which the present invention offers an improved tradeoff of sensitivity vs. false defects and nuisance defects.

Consider Table 1 from the viewpoint of a system in which defects are found by looking only at the difference signals in Detector A and Detector B independently. Ignore, for a moment, the values entered within the cells of the matrix; think of the lower right cell, for example, as signifying only the condition in which the difference signal from Detector A is 10 and the difference signal from Detector B is 10, as if the cell were empty. The bold lines which cross near the center of the matrix indicate that the operator selected a defect threshold of 6 for Detector A and also a defect threshold of 6 for Detector B. Those bold lines divide the array into four quadrants. In the upper left quadrant, neither detector reported a defect. In the lower right quadrant, both detectors reported a defect. In the upper right quadrant, onlydetector A reported a defect. In the lower left quadrant, only detector B reported a defect.

TABLE 1

How the Present Invention Can Reduce the Rate of False/Nuisance Defects Without Compromising Sensitivity

| Difference Signal in Detector B | Difference Signal (DS) in Detector A | | | | | | | | | |
|---|---|---|---|---|---|---|---|---|---|---|
| | 1 | 2 | 3 | 4 | 5 | 6 | 7 | 8 | 9 | 10 |
| 1 | 1.41 | 2.24 | 3.16 | 4.12 | 5.10 | 6.08 | *7.07* | *8.06* | 9.06 | 10.05 |
| 2 | 2.24 | 2.83 | 3.61 | 4.47 | 5.39 | 6.32 | *7.28* | *8.25* | 9.22 | 10.20 |
| 3 | 3.16 | 3.61 | 4.24 | 5.00 | 5.83 | 6.71 | *7.62* | 8.54 | 9.49 | 10.44 |
| 4 | 4.12 | 4.47 | 5.00 | 5.66 | 6.40 | 7.21 | *8.06* | 8.94 | 9.85 | 10.77 |
| 5 | 5.10 | 5.39 | 5.83 | 6.40 | 7.07 | 7.81 | 8.60 | 9.43 | 10.30 | 11.18 |
| 6 | 6.08 | 6.32 | 6.71 | 7.21 | 7.81 | 8.49 | 9.22 | 10.00 | 10.82 | 11.66 |
| 7 | *7.07* | *7.28* | *7.62* | *8.06* | 8.60 | 9.22 | 9.90 | 10.63 | 11.40 | 12.21 |
| 8 | *8.06* | *8.25* | 8.54 | 8.94 | 9.43 | 10.00 | 10.63 | 11.31 | 12.04 | 12.81 |
| 9 | 9.06 | 9.22 | 9.49 | 9.85 | 10.30 | 10.82 | 11.40 | 12.04 | 12.73 | 13.45 |
| 10 | 10.05 | 10.20 | 10.44 | 10.77 | 11.18 | 11.66 | 12.21 | 12.81 | 13.45 | 14.14 |

Now consider Table 1 from the standpoint of a preferred embodiment of the present invention. The cells within the matrix of Table 1 contain the composite difference signals for the various values, computed by squaring the row heading and the column heading, adding the tow squares, and taking the square root of the sum.

By selecting a defect threshold of 8.50, one method of this invention would unambiguously fine as non-defects the twelve cells in Table 1 which are shaded gray. Table 1 illustrates how the method of the present invention improves the tradeoff between sensitivity vs. false defects and nuisance, in this case by making it possible to reduce the rate of false and nuisance defects without compromising sensitivity.

In the context of Table 1, another advantage of the present invention is that it would unambiguously report all the non-shaded cells in the upper right and lower left quadrants as defects.

Table 2 is identical to Table 1 in every respect except that the shading appears in different cells, as a result of choosing a different threshold.

TABLE 2

How the Present Invention Can Enhance Sensitivity Without Increasing the False/Nuisance Defect Rate

| Difference Signal in Detector B | Difference Signal (DS) in Detector A | | | | | | | | | |
|---|---|---|---|---|---|---|---|---|---|---|
| | 1 | 2 | 3 | 4 | 5 | 6 | 7 | 8 | 9 | 10 |
| 1 | 1.41 | 2.24 | 3.16 | 4.12 | 5.10 | 6.08 | 7.07 | 8.06 | 9.06 | 10.05 |
| 2 | 2.24 | 2.83 | 3.61 | 4.47 | 5.39 | 6.32 | 7.28 | 8.25 | 9.22 | 10.20 |
| 3 | 3.16 | 3.61 | 4.24 | 5.00 | 5.83 | 6.71 | 7.62 | 8.54 | 9.49 | 10.44 |
| 4 | 4.12 | 4.47 | 5.00 | 5.66 | 6.40 | *7.21* | 8.06 | 8.94 | 9.85 | 10.77 |
| 5 | 5.10 | 5.39 | 5.83 | 6.40 | *7.07* | *7.81* | 8.60 | 9.43 | 10.30 | 11.18 |
| 6 | 6.08 | 6.32 | 6.71 | *7.21* | *7.81* | *8.49* | 9.22 | 10.00 | 10.82 | 11.66 |
| 7 | 7.07 | 7.28 | 7.62 | 8.06 | 8.60 | 9.22 | 9.90 | 10.63 | 11.40 | 12.21 |
| 8 | 8.06 | 8.25 | 8.54 | 8.94 | 9.43 | 10.00 | 10.63 | 11.31 | 12.04 | 12.81 |
| 9 | 9.06 | 9.22 | 9.49 | 9.85 | 10.30 | 10.82 | 11.40 | 12.04 | 12.73 | 13.45 |
| 10 | 10.05 | 10.20 | 10.44 | 10.77 | 11.18 | 11.66 | 12.21 | 12.81 | 13.45 | 14.14 |

As an example, by selecting a defect threshold of 7.0, one method in accordance with the present invention could unambiguously define as defects the six cells in Table 2 which are shaded gray. Table 2 illustrates how the method of the present invention improves the tradeoff between sensitivity vs. false defects and nuisance, in this case by making it possible to set a defect threshold which enhances sensitivity without increasing the rate of false defects.

FIG. 7 illustrates a defect threshold 701 which has the shape of an ellipse, with false or nuisance defects 702 inside the ellipse 701 and real defects 703 outside the ellipse 701. In most cases, an elliptical defect threshold would represent an improvement because one detector usually has more noise than another. A higher level of noise in a detector implies the need for a higher defect threshold in order to minimize false defects. In FIG. 7, the horizontal orientation of the ellipse 701 implies that Detector B has a higher level of noise than Detector A. If Detector A had a higher level of noise than Detector B, the ellipse would have a vertical orientation.

Figure 8:
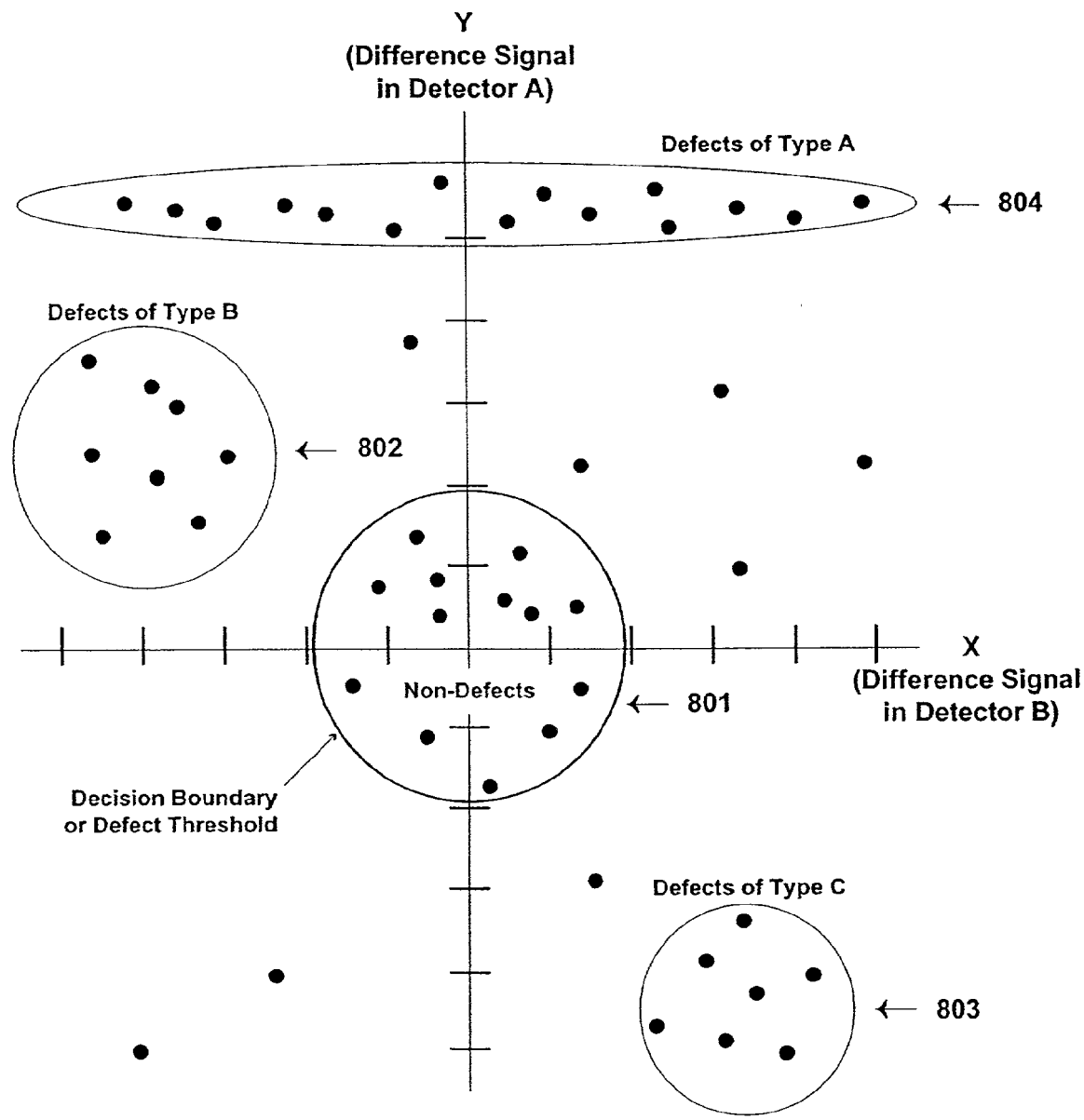
FIG. 8 illustrates a two-dimensional scatter plot showing that it is possible to draw a plurality of defect thresholds within the defect area to classify defects of certain types.

FIG. 8 illustrates yet another advantage of our novel method, namely the ability to classify defects according to the area where they appear in the two-dimensional plot. Defects of specific types will repeatedly cluster in specific regions. FIG. 8 contains not only a defect-threshold circle 801 with its center at the origin, but also two other circles 802 and 803 and an elongated ellipse 804. Defects which lie within the two circles 802 and 803 and the elongated ellipse 804 are likely to be of specific defect types (here listed as Type A, Type B, and Type C). As a result, the inspection system will be able to classify defects automatically on the basis of their position in the plot, thereby giving engineers in the wafer fab or mask shop clues as to how to refine their manufacturing process to eliminate those defects. The types of defects which tend to cluster in specific areas in the plot will depend on the individual manufacturing process; engineers in the wafer fab or mask shop will have to identify them empirically.

Figure 9:
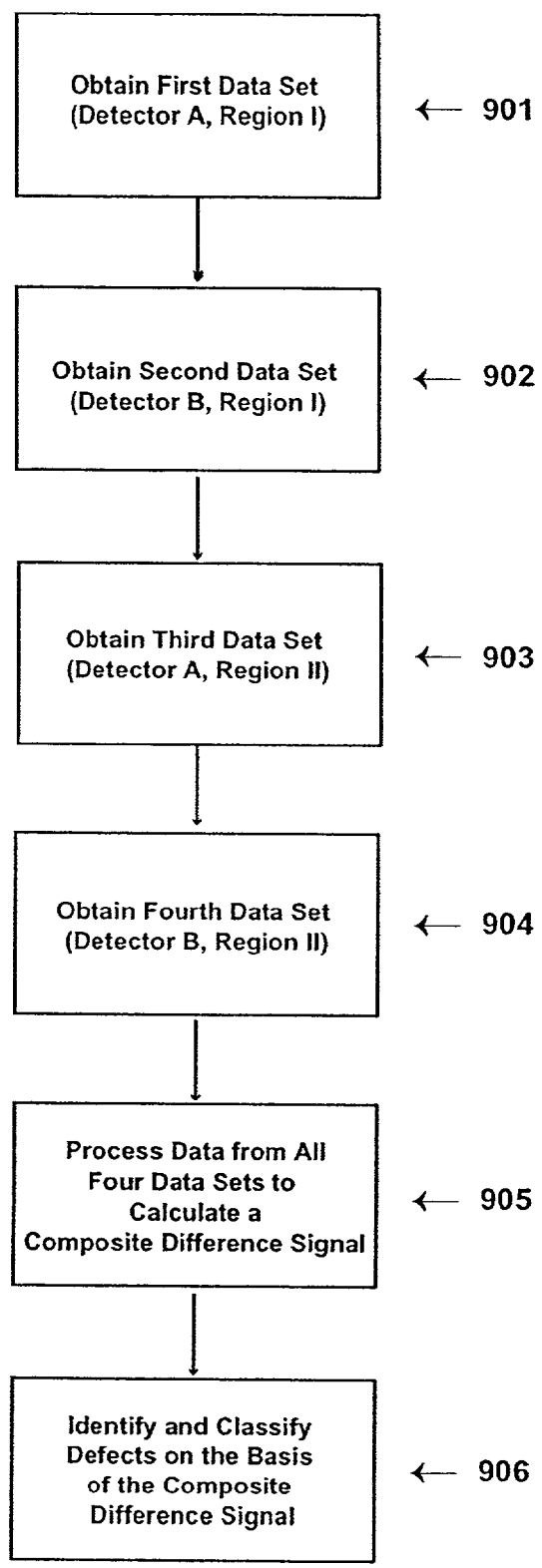
FIG. 9 illustrates a novel method for classifying defects.

We disclose the following novel method, shown in FIG. 9, of identifying and classifying defects on a substrate by exposing the substrate with a beam of charged particles in an inspection system which contains at least two detectors, comprising the following six steps:

Detector A obtains a set of image data from Region I (901),

Detector B obtains a set of image data from Region I (at least a portion of it) (902), Detector A obtains a set of image data from Region II (903), Detector B obtains a set of image data from Region II (at least a portion of it) (904), the inspection system processes the data from all four data sets to calculate a composite difference signal (905), and the inspection identifies and classifies the defects as being of a certain type on the basis of the composite difference signal (906).

Array Mode with Two Detectors

Figure 10:
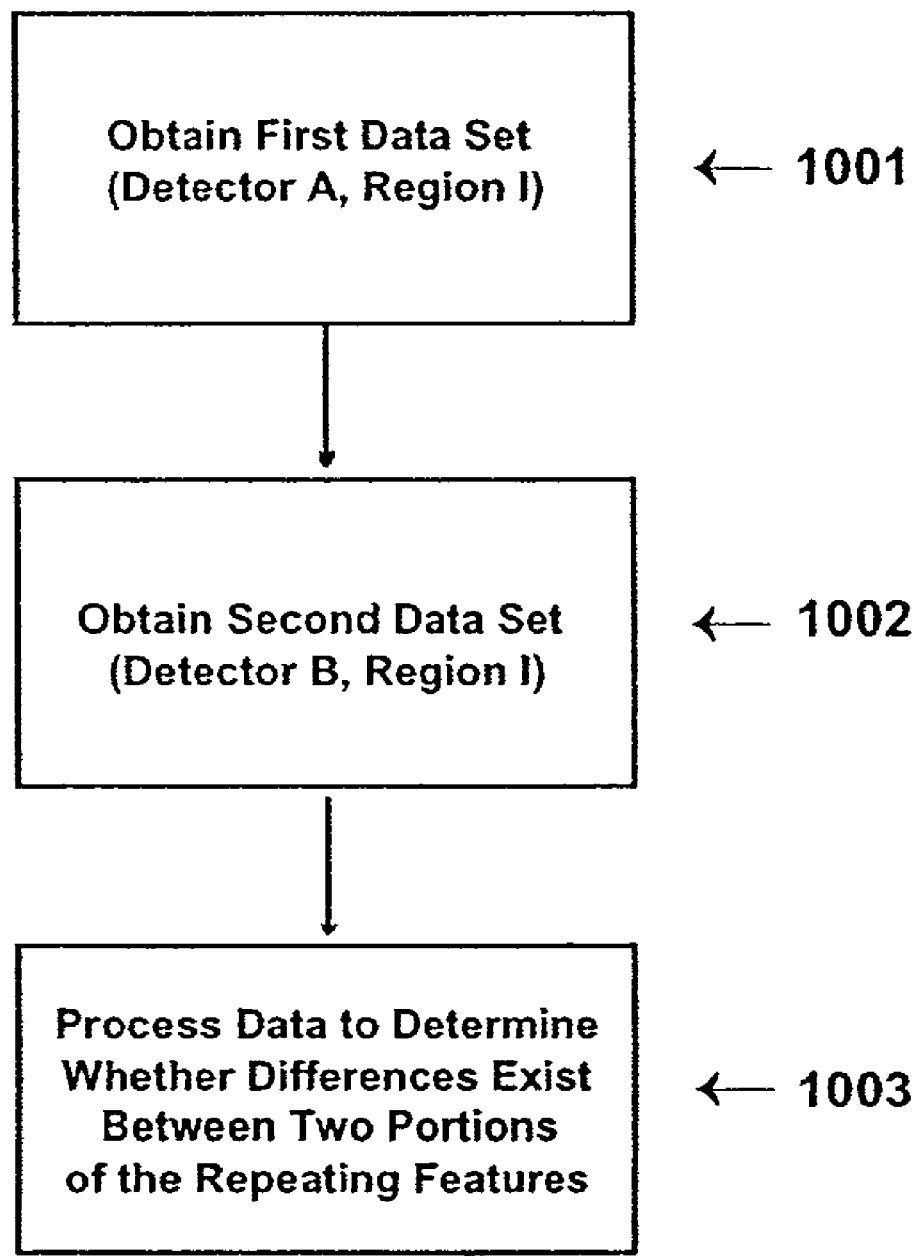
FIG. 10 illustrates a novel method for inspection in array mode with two detectors.

FIG. 10 illustrates a novel method of inspecting and/or characterizing a substrate in an array mode, in which each of two detectors collects image data from a single die that contains a plurality of substantially identical features, which we will refer to as "cells." For example, the substrate might be a DRAM chip, a DRAM photomask for exposing DRAM chips, or any of a wide variety of wafers and photomasks which contain an array of repeating patterns. In array mode, the test image and the reference image consist of nominally identical cells within the same region (where a region might be a semiconductor die) on one substrate. The method consists of collecting image data from two nominally identical cells with each of two detectors to look for differences between the cells. It encompasses the following three steps:

Detector A obtains a set of image data from Region I, where Region I is a die which contains an array of substantially repeating features (1001), Detector B obtains a set of image data from Region I (at least a portion of it) (1002), and the inspection system processes the data to determine whether differences exist between a first portion of the repeating features and a second portion of the repeating features (1003).

In step 1003, the inspection system might process simultaneously all four sets of image data within Region I: image data from a first cell collected by Detector A, image data from a second cell collected by Detector A, image data from a first cell collected by Detector B, and image data from a second cell collected by Detector B. The comparisons would reveal either differences between the nominally identical regions or nonrepeating portions within the array.

To determine which of the differences are truly defects, rather than false defects or nuisance defects, the system could use the method described earlier: calculate the difference signal for each pixel with Detector A, calculate the difference signal for each pixel with Detector B, perform a mathematical operation on the two difference signals, and compare the sum with a difference threshold.

Array Mode With One Detector

Figure 11:
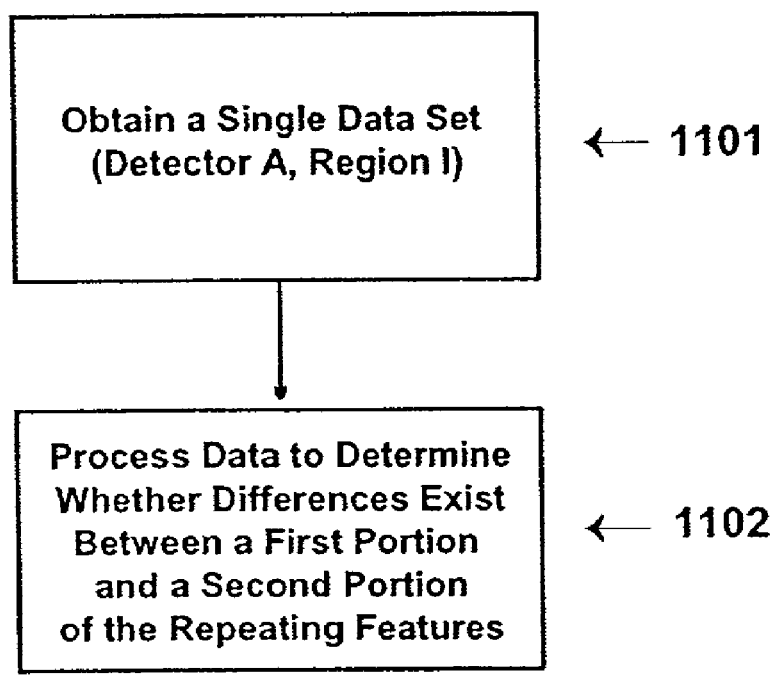
FIG. 11A illustrates a novel method for inspection in array mode with one detector.
FIG. 11B illustrates an apparatus which could be used to implement the method of FIG. 11A.
FIG. 11C illustrates a system with a segmented detector.
FIG. 11D illustrates a simple split detector.
FIG. 11E illustrates a system including a more complex split detector.
Figure 11:
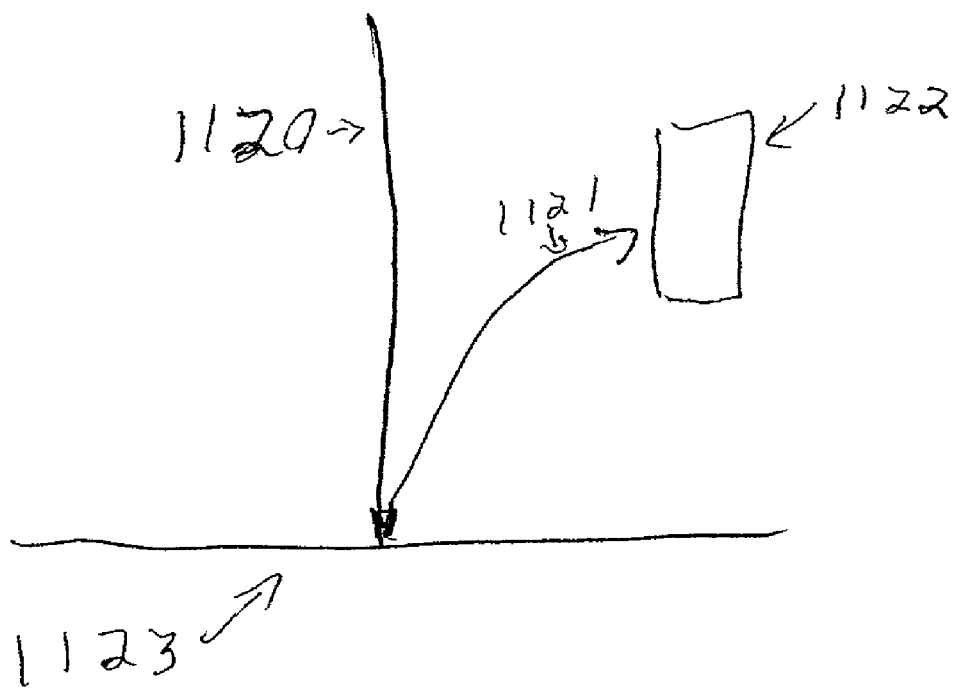

In some cases, it would be useful to complete an array mode inspection to look for defects with only one detector. For example, if the purpose of the inspection were to detect particles or microscratches, a single side-mounted detector might provide sufficient information. The field of view of a single detector is large enough to capture image data for more than one cell at a time. In this case, the inspection would consist of only two steps (FIG. 11):

Detector A obtains a set of image data from a die which contains an array of substantially repeating features (1101), and the inspection system processes the data to determine whether differences exist between a first portion of the repeating features and a second portion of the repeating features (1102).

In step 1102, the system would compare the image data for two nominally identical cells within that same data set.

Figure 11C:
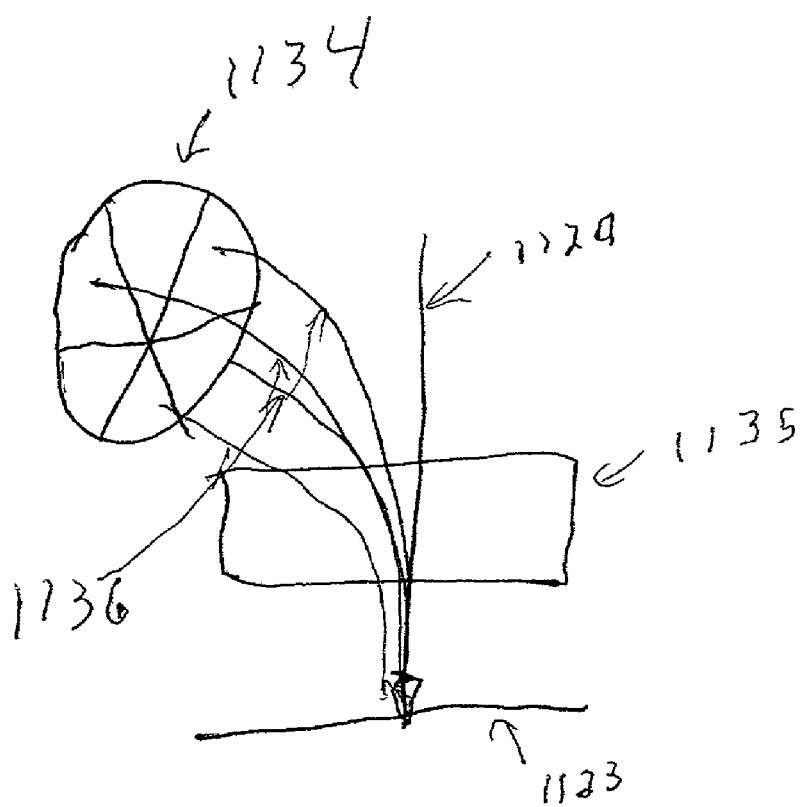

FIG. 11B illustrates an apparatus of an embodiment of the invention using at least one detector. In this apparatus, electrons from an incident beam 1120 impinge upon a substrate 1123. Secondary electrons 1121 are emitted from the substrate 1123 and detected by detector 1122. In a variation on this embodiment, as shown in FIG. 11C, detector 1134 is a segmented detector, and may be used to provide additional information concerning the substrate, since different portions of the segmented detector may be used to detect electrons 1136 having differing trajectories. The differing trajectories may be the result of the topographic features, or could be the result of differing energies if an energy prism (not shown) is placed before or after the Wien Filter 1135. Such an arrangement could be used instead of or in addition to the detector 1122 of FIG. 11B, or could be used in other embodiments of this invention.

There are a number of ways in which a segmented detector, such as detector 1134 shown in FIG. 11C, could be used. For example, a split detector shown in FIG. 11D with sectors 1191 and 1192 could be used to preferentially detect electrons launched to one side or the other from the sample. Secondary electrons tend to be emitted normal to surfaces. Therefore, topographical features on surfaces tend to emit secondary electrons in a non-isotropic manner. By subtracting the signal of one segment of the detector from that of another, the nontopographic details (such as material contrast) will be suppressed, and topographic variation will be enhanced. The detector could be segmented into quadrants (to look at higher order anisotropies of electron emission or to simultaneously act as split detectors along two axes), or split into even finer segments. Split annular detectors could also be used.

It is also possible to use a position sensitive detector ("PSD") with continuous or quasi-continuous position sensitivity. For example, a "linear PSD" or a 1D array detector could be used. Alternatively, a detector having continuous or quasi-continuous position sensitivity in all directions, such as a 2D array detector or microchannel plate could be used. In still another alternative implementation, the detectors could be physically separated (as mentioned elsewhere in more detail in this application) and signals from the detectors could be subtracted to enhance topographic contrast, while enhancing material contrast.

The detectors or detector elements could be photodiodes, electron multipliers, microchannel plates, or any other suitable electron detectors. Alternatively, the electrons could be first converted to photons by use or a scintillator or other device and then the photons could be detected with a CCD, TDI sensor, PMT or other suitable device.

In yet another alternative embodiment, the signals from the segments and/or from physically separate detectors could be combined in different ways as part of the same inspection, measurement or defect review step. For example, the signals could be both subtracted to create a "dark field" signal with enhanced topographic contrast, or combined to create "bright field" signal with enhanced material contrast. If desired, a linear (or nonlinear) combination of the bright field and dark field signals and/or the signals from the detectors or segments could be combined to create a "gray field" signal that has a selected degree of material contrast and a selected degree of topographic contrast. Any or all of these combinations of signals could be done while the signals are in analog format, or after they are digitized.

Figure 11E:
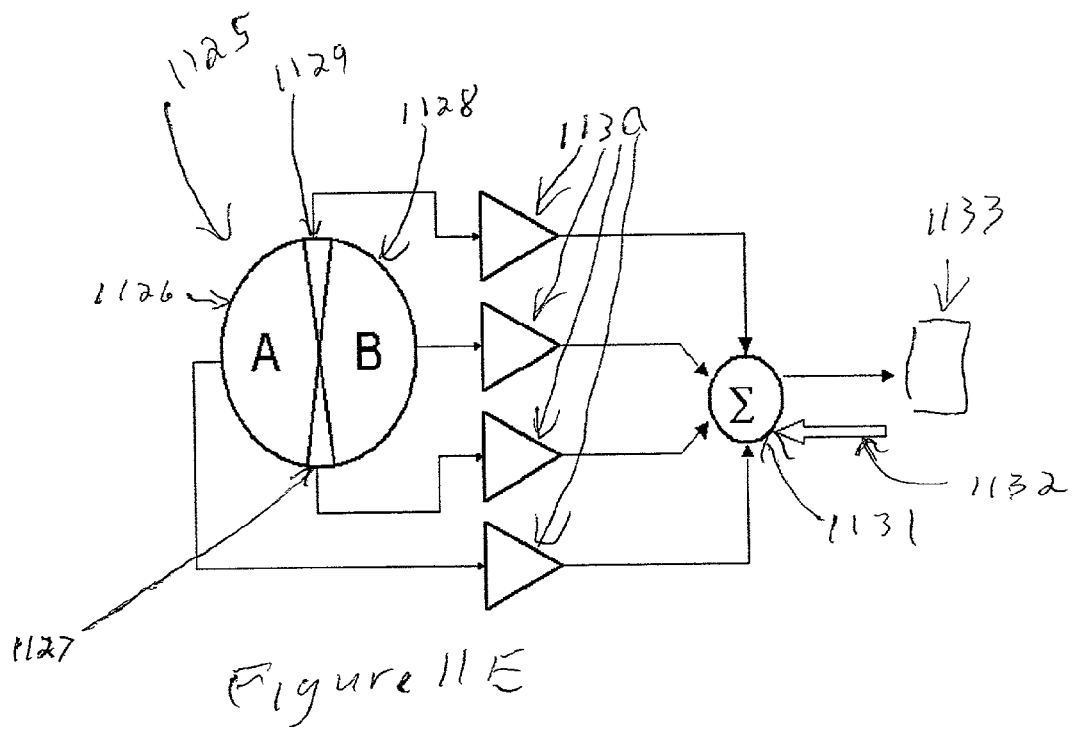
Figure 11D:
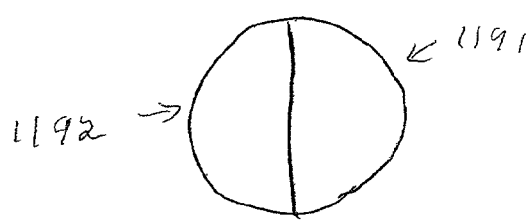

Circuitry that could be used for making this combination is shown in FIG. 11E. In this figure, a quadrant detector 1125 has four sectors 1126, 1127, 1128 and 1129. Sectors 1126 and 1128 have a relatively large area as compared to the other two sectors. Signals from each of these sectors are then preferably sent to video preamplifiers 1130, and combined in an analog video combiner 1131. Control signals 1132 control the combination performed by combiner 1131. The resulting combined signal can then be sent on to a video amplifier 1133. The signal can then be digitized, and further processing may be performed. Examples of such further processing are described elsewhere herein, and may also or instead be performed as described in U.S. Pat. No. 5,502,306, which is incorporated by reference herein.

In one embodiment of the invention, signals from sectors 1127 and 1129 are switched between signals from sectors 1126 and 1128 (or switched out of the circuit) to adjust the relative direction of the "split" on a split detector.

In a scanning electron beam system, the beam is scanned across the substrate. This can result in the "spot" of secondary electrons being scanned across the detector as the primary beam is scanned. The size of the spot may also change depending on various settings of the primary beam (such as beam landing energy at the sample). To better deal with this, the secondary electrons may be descanned and /or focused at the detector. However, this may not be necessary in a system with a split or otherwise segmented detector. If desired, performance may be improved by aligning the split along the direction of the secondary scan on the detector If aligning the scan to the split is desired, there are several ways in which this may be accomplished. For example, a mask may be placed in front of the detector an/or by rotating the detector itself. It may instead or additionally be accomplished by rotating the secondary beam (e.g., with a weak solenoidal lens), by deflecting the secondary beam (e.g with electric or magnetic deflectors) and/or by simultaneously changing the primary and secondary beam properties to affect the secondary scan direction. Alternatively, if the detector is made of many small segments (such as narrow angular "pie-slice" shaped segments), the segments may be switched and combined to create one or more large segments. This has the effect of rotating the direction of the detector's split without physically rotating the detector itself.

Alternatively, a position sensitive detector could be used even if not segmented. For example, an annular detector could be used to preferentially detect electrons launched at large angles from the sample.

In another preferred embodiment of this invention, a detector such as those described in FIG. 11b through 11E, or elsewhere herein, is placed to detect electrons as they appear at the pupil plane in a multipixel inspection system. Such inspection systems are described in U.S. Pat. No. 6,087,659 and Published PCT Application WO0188514. This could be in addition to detection at the image plane shown therein, to provide additional data for defect inspection, review and/or classification.

If desired, filtering of the electrons could be performed before detection, to remove backscattered electrons and detect only secondary electrons. In one embodiment, backscattered electrons are detected at another detector and signals therefrom could be analyzed to obtain composition data, e.g., from the atomic weight, concerning the substrate.

Figure 12:
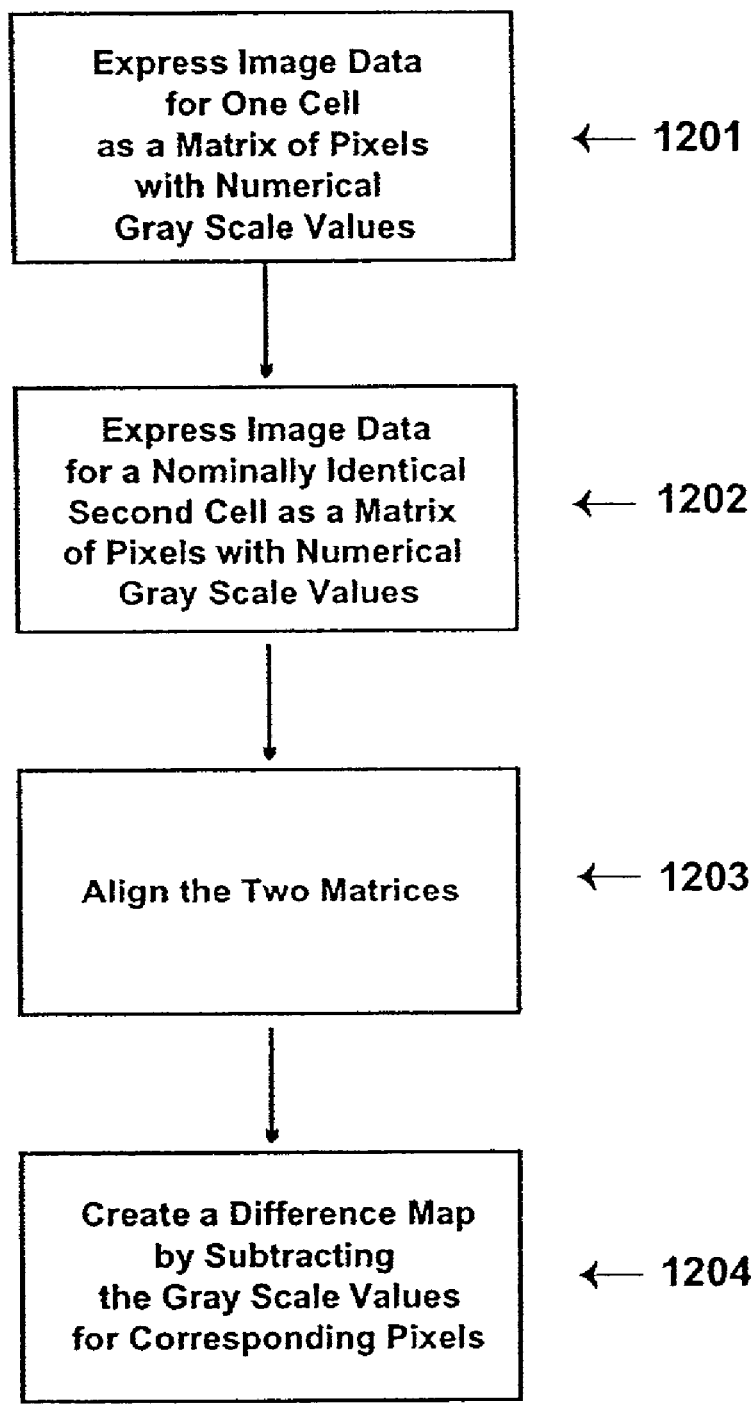
FIG. 12 illustrates a novel "shift-and-subtract" method for processing data during an inspection in array mode.

FIG. 12 illustrates one possible implementation of the inspection process. In this embodiment, the inspection system could process the data in either of two different ways. One method would be a "shift-and-subtract" technique, which involves the following steps express the image data for one cell on the die as a matrix of pixels with numerical gray scale values in step 1201, express the image data for a nominally identical second cell on the same die as a matrix of pixels with numerical gray scale values in step 1202, align the two matrices to ensure that the analogous places in the two matrices contain the gray scale values for corresponding pixels in the nominally identical cells in step 1203, and create a difference map by subtracting the gray-scale values for corresponding pixels in step 1204.

The differences will appear as bright areas in the difference map. Brighter areas are more likely to be defects.

The method illustrated in FIG. 12 and described in steps 1201 through 1204 would also be a suitable method of processing data during step 1003 of the novel method illustrated in FIG. 10 (array mode inspection with two detectors).

The second method of processing the data in an array-mode inspection with only one detector involves a Fourier transform. As with the previous method, the purpose of this technique is to find defects. But rather than looking for differences, this technique identifies non-repeating patterns within the array. It consists of the following three steps (FIG. 13):

> transform the image data from the spatial domain into the frequency domain (1301),
>
> filter the Fourier transform in the frequency domain to remove at least a portion of the repeating pattern in the spatial domain (1302), and
>
> perform an inverse transform of the transformed image (1303).

The techniques for Fourier transform are well known, and their use in inspection of semiconductor wafers or masks is described in U.S. Pat. No. 6,021,214, which is incorporated herein by reference. In the frequency domain, it is straightforward to remove repeating features. After removing them, the non-repeating features, which are candidates for defects, appear as dark features against a gray background.

Figure 13:
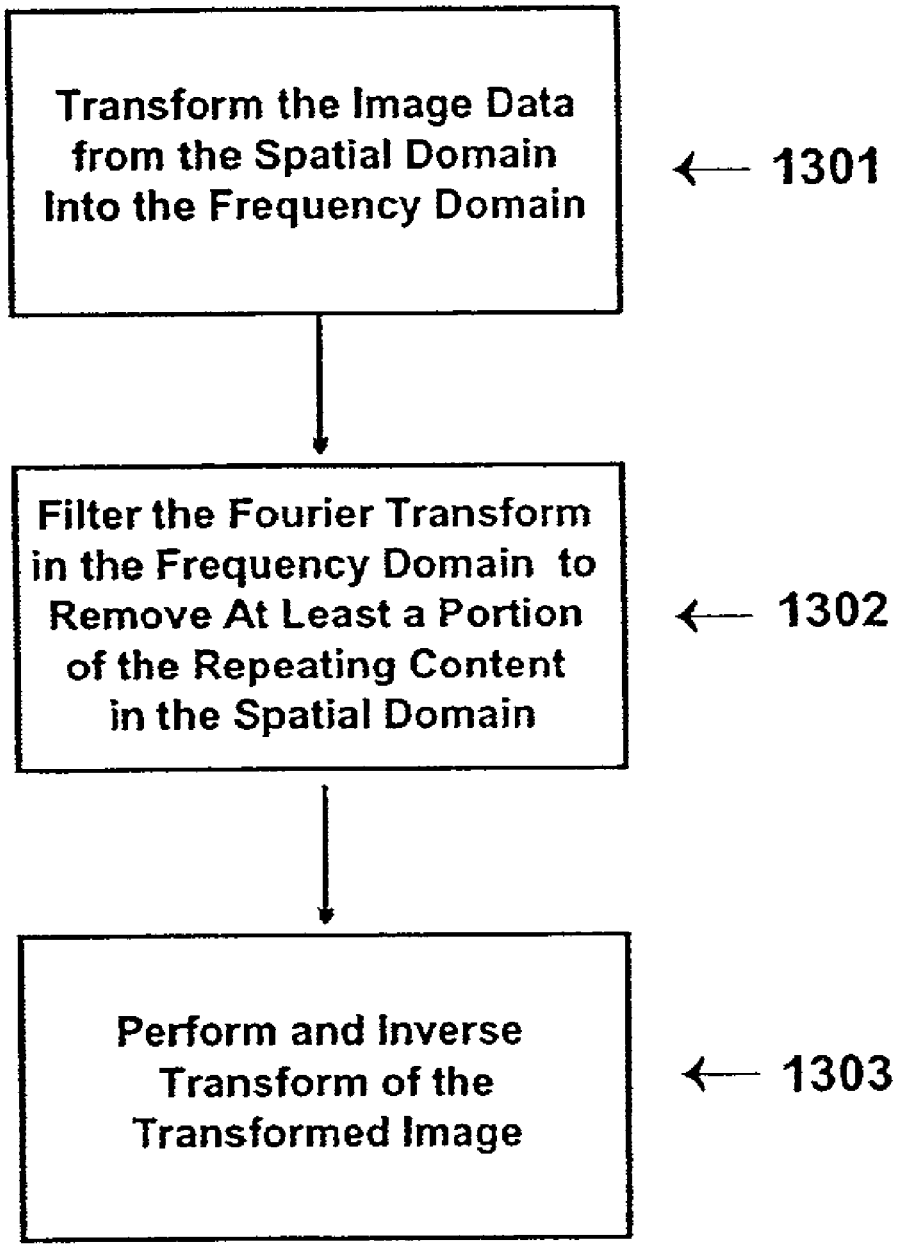
FIG. 13 illustrates a novel method for processing data via a Fourier transform during an inspection in array mode.

This method of processing data in an array-mode inspection illustrated in FIG. 13 and described in steps 1301 through 1303 would also be a suitable method of processing data during step 1003 of the novel method illustrated in FIG. 10 (array mode inspection with two detectors).

Array mode inspections with a single detector are useful for inspecting a substrate anew, for redetecting a defect already found by another inspection system (such as an optical inspection system, which has lower resolution than an electron-beam system), or for classifying defects into different types.

All the array mode inspection methods described above are useful for inspecting a substrate anew, for redetecting a defect already found by another inspection system (such as an optical inspection system, which has lower resolution than an electron-beam system), or for classifying defects into different types.

Inspection Alone in Array Mode or Die-to-Die Mode

Figure 14:
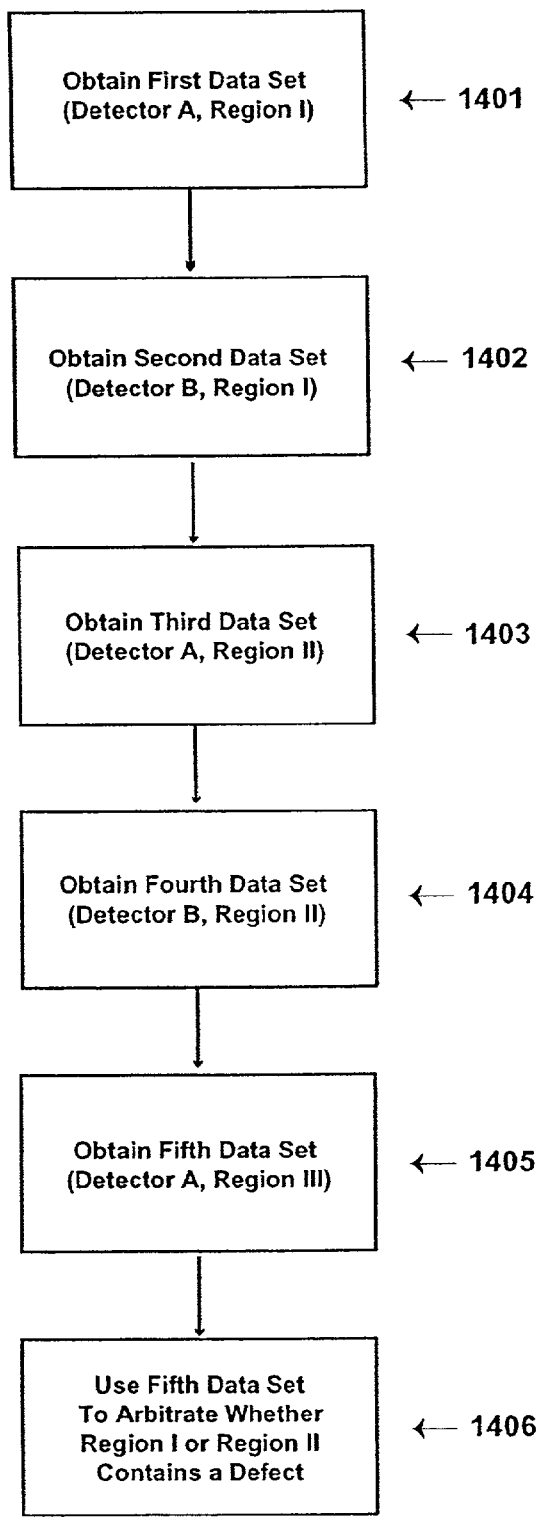
FIG. 14 illustrates a novel method for inspecting a substrate with arbitration in array mode or in die-to-die mode.

The following method, shown in FIG. 14, is appropriate for inspecting a substrate in array mode, where the substrate contains a plurality of substantially identical features. Methods described in the previous sections for inspecting in array mode or in die-to-die mode can reveal differences or non-repeating patterns in nominally identical regions, but an automated system can have difficulty determining which of the two regions is correct and which is defective. This method solves that problem with the following six steps:

> Detector A obtains a set of image data from Region I (1401),
>
> Detector B obtains a set of image data from Region I (at least a portion of it) (1402),
>
> Detector A obtains a set of image data from Region II (1403),
>
> Detector B obtains a set of image data from Region II (at least a portion of it) (1404),
>
> Detector A takes an image of Region III (1405), and
>
> the inspection system uses the image data from Region III to arbitrate which of Region I or Region II contains a defect (1406).

This method would apply in situations where the inspection system locates a difference between Region I and Region II by comparing the image data collected during steps 1401, 1402, 1403, and 1404, but cannot discern whether the defect lies in Region I or Region II. In step 1406, the system compares the image data from both Region I and Region II with the image data from Region III. If the image data from Region I matches the image data from Region III, then the defect resides in Region II. But if the image data from Region II matches the image data from Region III, then the defect resides in Region I.

Redetection Alone in Array Mode or Die-to-Die Mode

Figure 15:
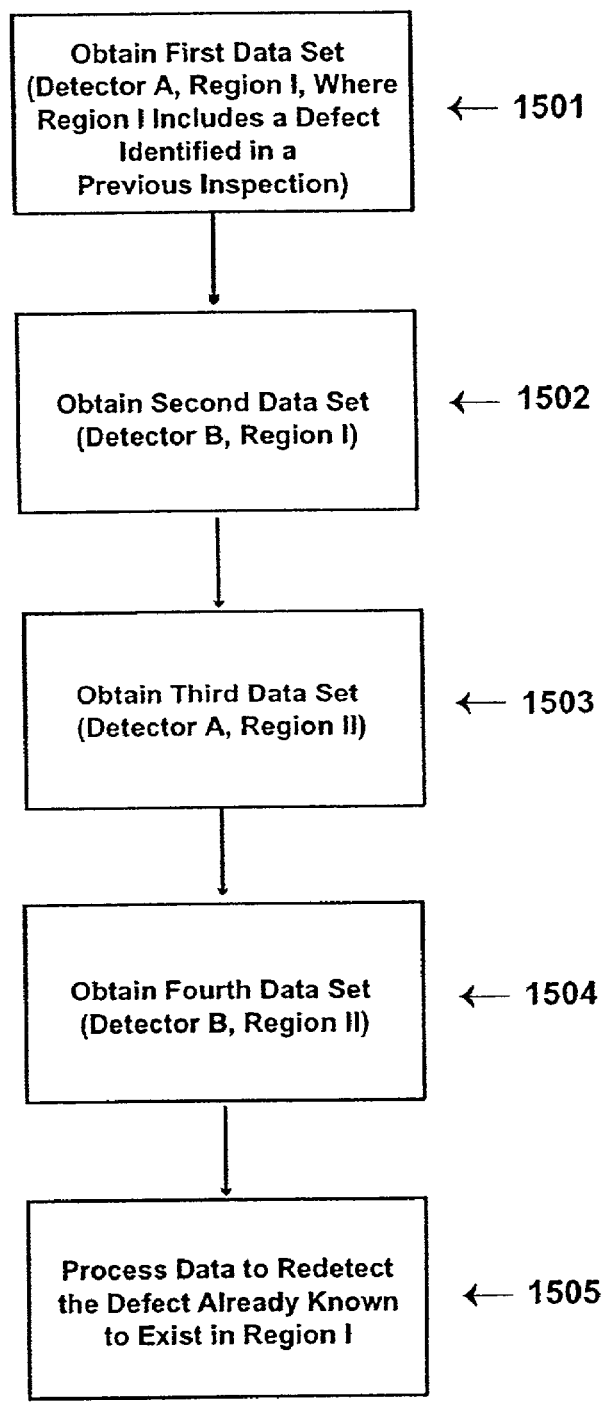
FIG. 15 illustrates a novel method of redetecting defects in array mode or in die-to-die mode.

The following method, shown in FIG. 15, is appropriate for redetecting defects or other features already found by another inspection system on a substrate with a plurality of substantially identical features. It exploits previous knowledge that a feature exists in a given region (for example, Region I). It encompasses the following four steps:

> Detector A obtains a set of image data from Region I (1501),
>
> Detector B obtains a set of image data from Region I (at least a portion of it) (1502),
>
> Detector A obtains a set of image data from Region II (1503),
>
> Detector B obtains a set of image data from Region II (at least a portion of it) (1504), and
>
> the inspection system processes the data from all four data sets to redetect the defect which is already known to exist in Region I (1505).

Both detectors will capture image data from a wide enough area to include the previously identified feature, even taking into consideration the fact that the stage coordinates contain some margin of error. The four sets of image data will provide enough information to generate a high-resolution image of the defect. Since the previous inspection has already revealed that the defect exists, and in which region it exists, there is no need to obtain image data from a third region (as in step 1406 of the previous method) to arbitrate which of Region I or Region II contains the defect.

A Moving Stage

Figure 16:
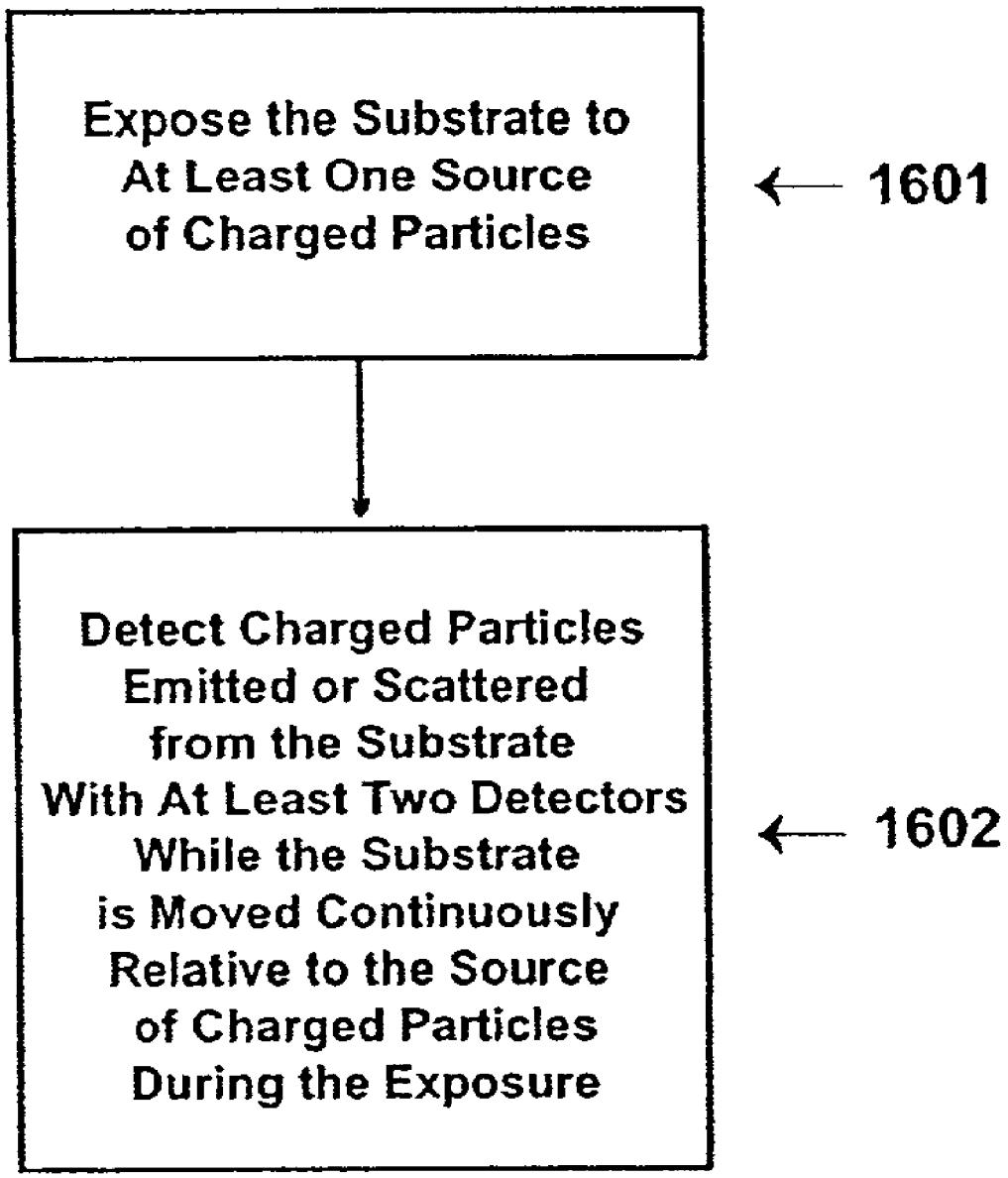
FIG. 16 illustrates a novel method of inspecting a substrate with a beam of charged particles with two detectors while the substrate moves with respect to the beam.

In many cases, it would be advantageous to position the substrate upon a stage that moves with respect to the charged particle beam. We disclose the following method, shown in FIG. 16A, of inspecting and/or characterizing substrates (e.g., semiconductor wafers, singulated die, package substrates, reticles or photomasks):

> expose the substrate to at least one source of charged particles (1601), and
>
> detect charged particles emitted from the substrate with at least two detectors while the substrate is moved continuously relative to the source of charged particles during the exposure (1602).

In most cases, the inspection would consist of exposing at least two portions of the substrate to the charged particles, detecting the charged particles emitted from those portions, and using data from the detectors to determine whether potential defects exist.

The charged particles would most commonly be electrons. In various situations, it may be advantageous to supply the electrons either with a flood illumination source or in a focused beam. The most convenient way of moving the substrate would be with a stage, which could move intermittently or continuously, either at a substantially constant velocity or at a changing velocity.

In different situations, it would be advantageous to position the two detectors so that they detect charged particles emitted from different ranges of azimuthal angles relative to the substrate; for example, to detect microscratches with particular orientations. In other situations, it would be advantageous to position the two detectors so that they detect charged particles emitted from different elevation angles relative to the substrate; for example, to detect primarily materials differences (from higher elevation angles) or microscratches (from lower elevation angles).

Figure 16B:
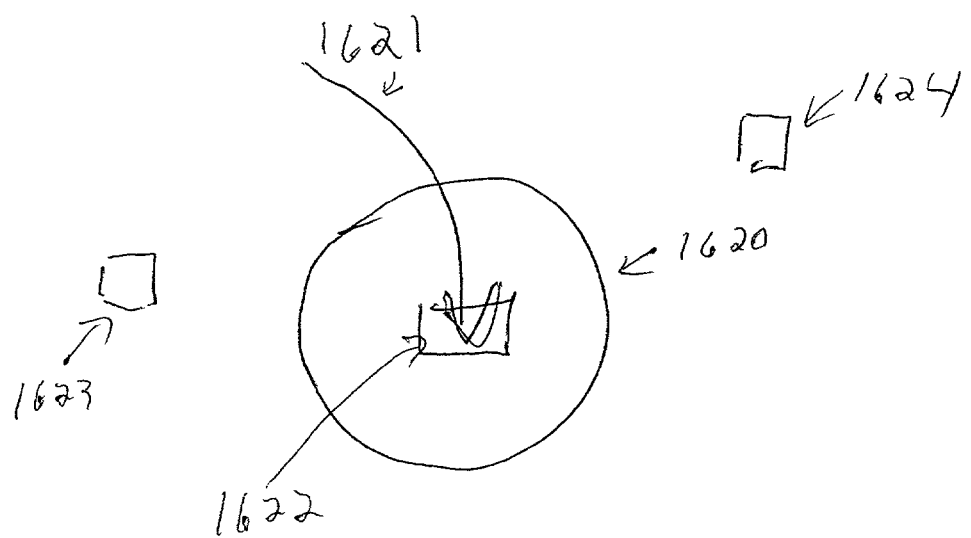
FIG. 16B illustrates a system with a moving stage.

FIG. 16B illustrates an embodiment in which a substrate is inspected while the substrate is moved with regard to an incident particle beam. In this Figure, electrons from incident beam 1621 impinge on substrate 1620. Substrate 1620 is moved relative to beam 1621 during this process. In a preferred embodiment, beam 1621 is scanned at an angle to the direction of that relative motion. This produces a scan area 1622 on substrate 1620. Secondary or backscattered electrons from substrate 1620 are detected by at least two detectors, illustrated as detectors 1623 and 1624. The resulting information may be processed by any technique, including prior art methods. However, it is preferably processed by the methods described in accordance with the present invention herein. Further details regarding an apparatus capable of producing the continuous relative motion of this embodiment may be found in U.S. Pat. No. 5,502,306, which is incorporated by reference herein.

X-Ray Detectors

In another method, the system contains an X-ray detector as well as two or more electron detectors. When an electron beam strikes a material, the material emits X-rays with an energy characteristic of that material. The inspection system can therefore identify the material in a specific area of the substrate on the basis of the X-ray energies, either by energy dispersive X-ray spectroscopy (EDX) or by wavelength dispersive spectroscopy (WDX).

Figure 17:
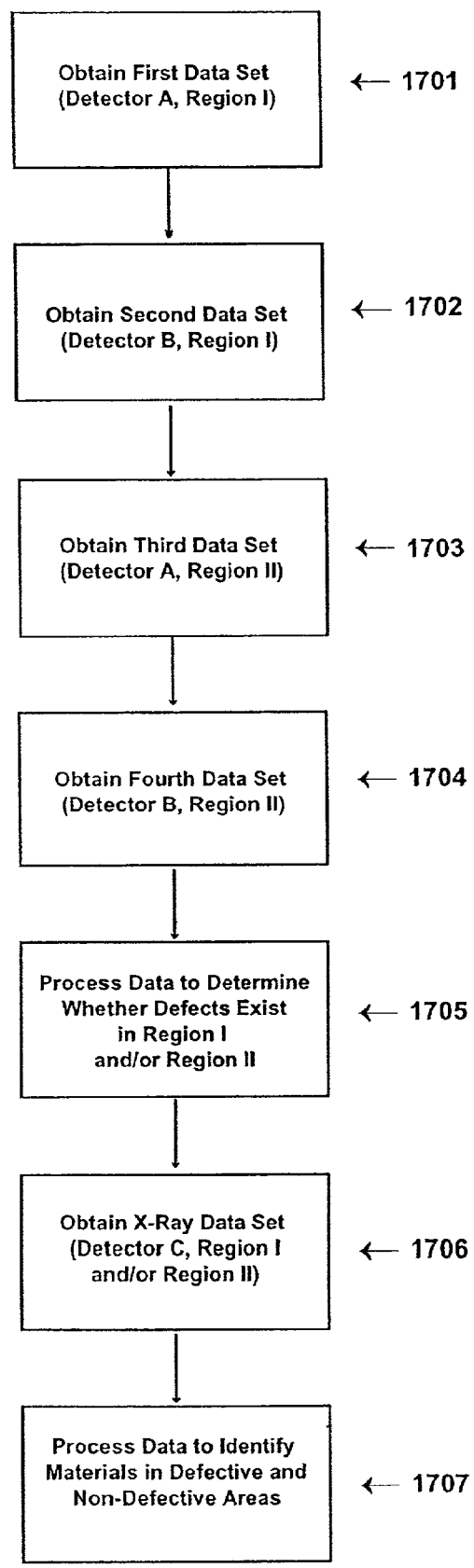
FIG. 17 illustrates a novel method of inspecting a substrate with an X-ray detector.
Figure 17A:
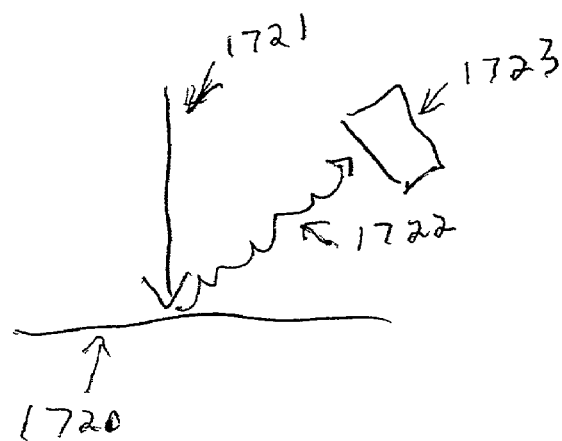
FIG. 17A illustrates an apparatus including an x-ray detector

An apparatus for inspecting a substrate with an x-ray detector is shown in FIG. 17A. In this Figure, electron beam 1721 impinges on substrate 1720. As a result, x-rays 1722 are emitted and detected by detector 1723. These x-rays are then processed as described in more detail herein.

It is possible to combine this method with any of the other methods of inspecting, redetecting, or classifying defects. For example, we disclose a novel method of inspecting a substrate in die-to-die mode which characterizes the material on the on the substrate while it detects defects. In this method, an inspection system exposes a substrate to either a flood or focused beam of electrons or other charged particles. The system then detects secondary electrons from that substrate with at least two electron detectors (Detector A and Detector B), which collect image data from two nominally identical die (Region I and Region II) on the same substrate. An X-ray detector (Detector C) detects X-rays emitted from the surface of the substrate. This method, shown in FIG. 17B, encompasses the following seven steps:

Detector A obtains a set of image data from Region I (1701),

Detector B obtains a set of image data from Region I (at least a portion of it) (1702), Detector A obtains a set of image data from Region II (1703), Detector B obtains a set of image data from Region II (at least a portion of it) (1704), the inspection system processes the data from the two data sets obtained by Detector A and the two data sets obtained by Detector B to determine whether a defect exists in either Region I or Region II (1705), Detector C obtains a set of image data from at least a portion of Region I and/or Region II (1706), and the inspection system processes the data from the data set obtained by Detector C to identify the materials in the defective and non-defective areas of Region I and/or Region II (1707).

Figure 18A:
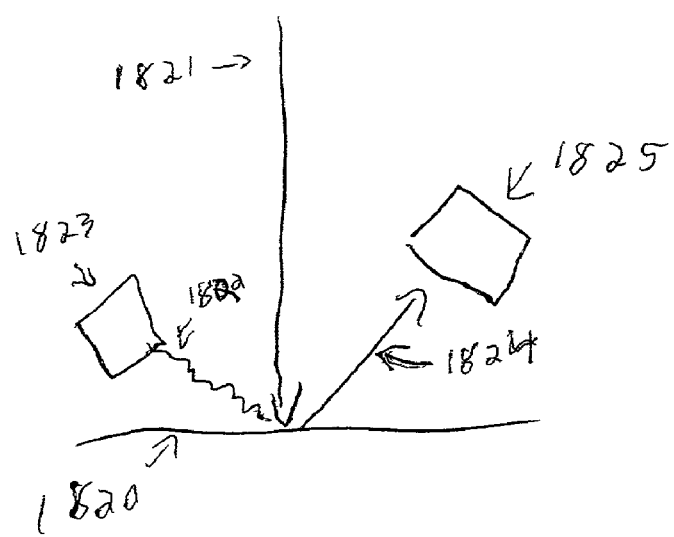
FIG. 18A illustrates an apparatus including an x-ray detector and an electron detector
Figure 18:
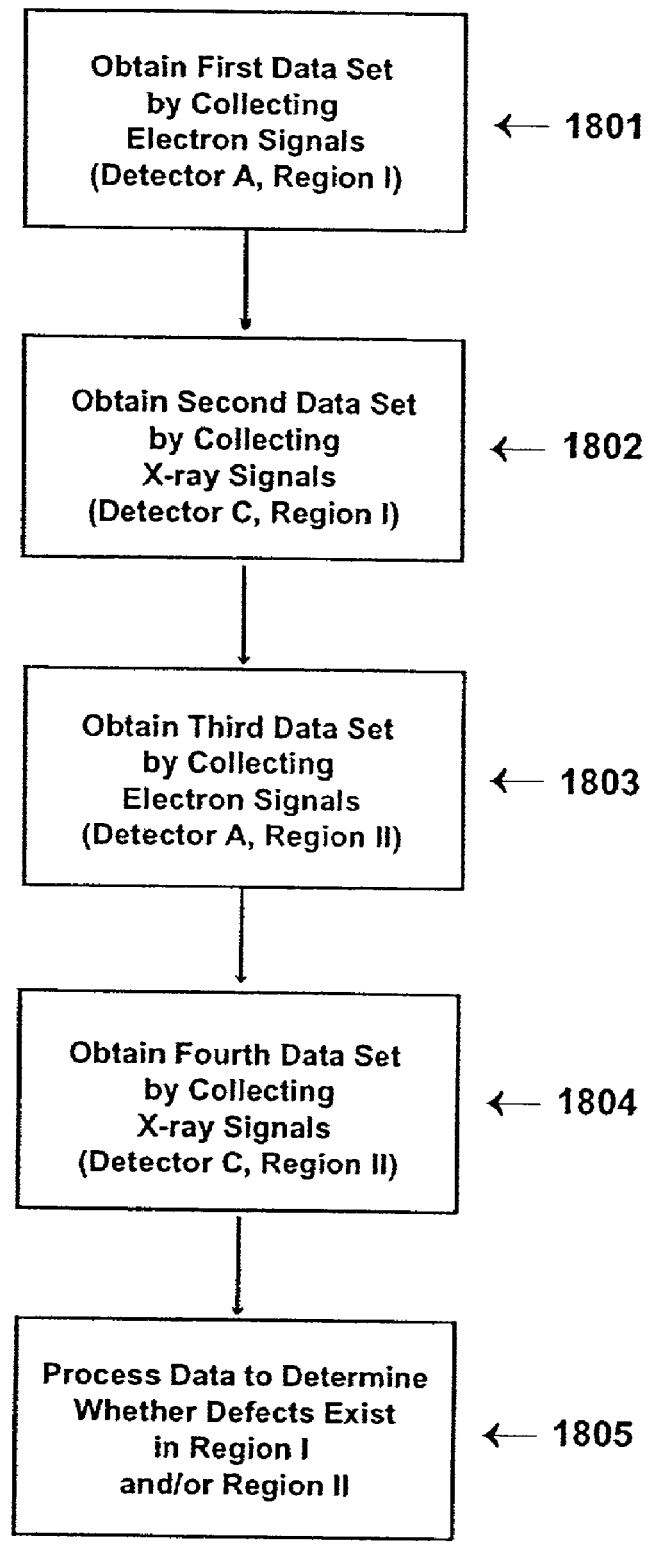
FIG. 18 illustrates a novel method of inspecting a substrate with at least two detectors, one of which is an X-ray detector.

An apparatus for inspecting a substrate with an x-ray detector is shown in FIG. 18A. In this Figure, electron beam 1821 impinges on substrate 1820. As a result, x-rays 1822 are emitted from the substrate and detected by detector 1823.

In addition, secondary or backscattered electrons 1824 are emitted from the substrate and detected by detector 1825. These x-rays and electrons are then processed as described in more detail herein.

In a simpler method, an inspection system exposes a substrate to either a flood or focused beam of electrons or other charged particles. The system then detects secondary electrons from that substrate with a single electron detector (Detector A) and with a single X-ray detector (Detector C). The detectors collect image data from two nominally identical die (Region I and Region II) on the same substrate. This method, shown in FIG. 18B, encompasses the following five steps:

Detector A obtains a set of image data from Region I (1801),

Detector C obtains a set of image data from Region I (at least a portion of it) (1802), Detector A obtains a set of image data from Region II (1803), Detector C obtains a set of image data from Region II (at least a portion of it) (1804), and the inspection system processes the data from all four data sets to determine whether a defect exists in either Region I or Region II and to identify the materials in the defective and non-defective areas of Regions I and/or Region II (1805).

Figure 19:
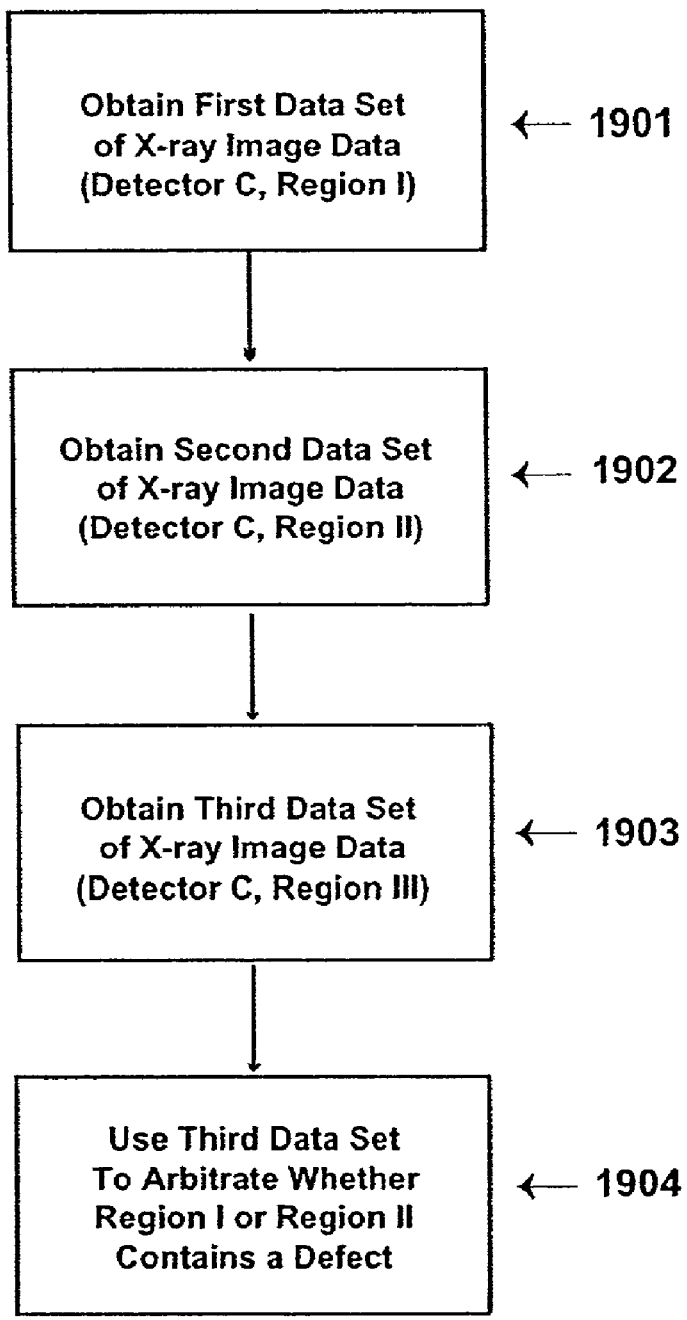
FIG. 19 illustrates a novel method of inspecting a substrate with a single X-ray detector.

In an even simpler method, the system conducts a die-to-die inspection with a single X-ray detector. The system relies on the differences in X-ray signals to detect defects. In this method, an inspection system exposes a substrate which contains a plurality of substantially identical features to either a flood or focused beam of electrons or other charged particles. The system then detects X-rays emitted from the surface of the substrate with a single X-ray detector (Detector C). Detector C collects image data from three nominally identical die (Region I, Region II, and Region III) on the same substrate. All three regions contain an array of substantially identical repeating features. This method, shown in FIG. 19, encompasses the following four steps:

Detector C obtains a set of image data from Region I (1901),

Detector C obtains a set of image data from Region II (1902),

Detector C obtains a set of image data from Region III (1903), and the inspection system uses the image data from Region im to arbitrate which of Region I or Region II contains a defect (1904).

This method would apply in situations where the inspection system locates a difference between Region I and Region II by comparing the image data collected during steps 1901 and 1902, but cannot discern whether the defect lies in Region I or Region II. In step 1904, the system compares the image data from both Region I and Region II with the image data from Region III. If the image data from Region I matches the image data from Region III, then the defect resides in Region II. But if the image data from Region II matches the image data from Region III, then the defect resides in Region I.

The preceding three methods show that it is possible to combine an X-ray detector with the other methods disclosed in this patent, all of which refer to die-to-die inspection mode. Many other combinations are possible, such as using an X-ray detector to inspect in array mode, in die-todatabase mode, to classify defects, etc. In the interest of brevity, we refrain from calling out all the possible combinations.

Die-to-Database Inspections

Figure 20:
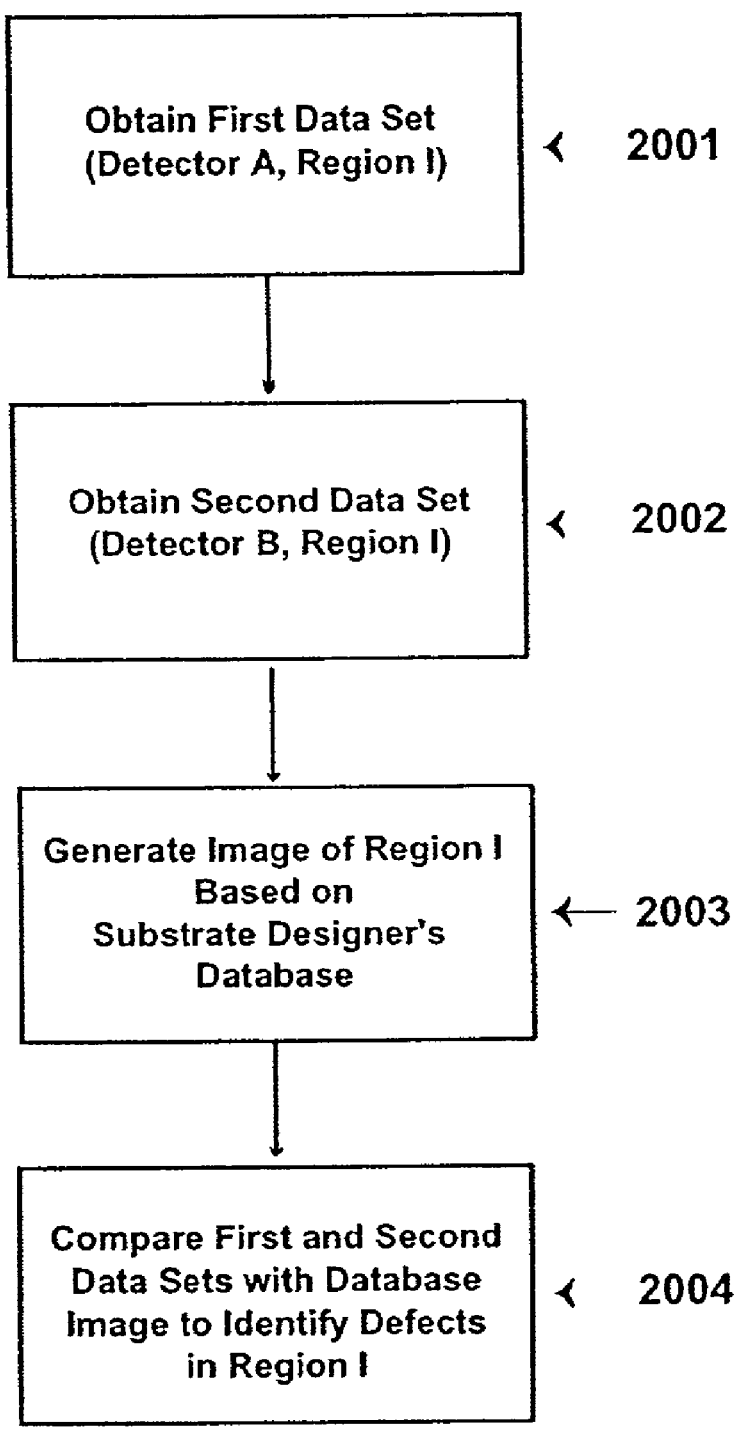
FIG. 20 illustrates a novel method of inspecting a substrate with two detectors in die-to-database mode.

In another method of inspecting a substrate (e.g., a patterned wafer, a singulated die, a reticle, or a photomask), the system compares image data acquired by two detectors with an image generated from the designer's database. In this method, known as die-to-database inspection, the system assumes the database image is correct, and it reports significant differences between the acquired image and the database image as defects on the substrate. We now disclose the novel method shown in FIG. 20A, which comprises the following four steps:

Detector A obtains a set of image data from Region I (2001),

Detector B obtains a set of image data from Region I (at least a portion of it) (2002), the inspection system generates an image of Region I based on the substrate designer's database (2003), and the inspection system compares the image data from Detector A and Detector B with the image based on the substrate designer's database to identify defects in Region I (2004).

Figure 20B:
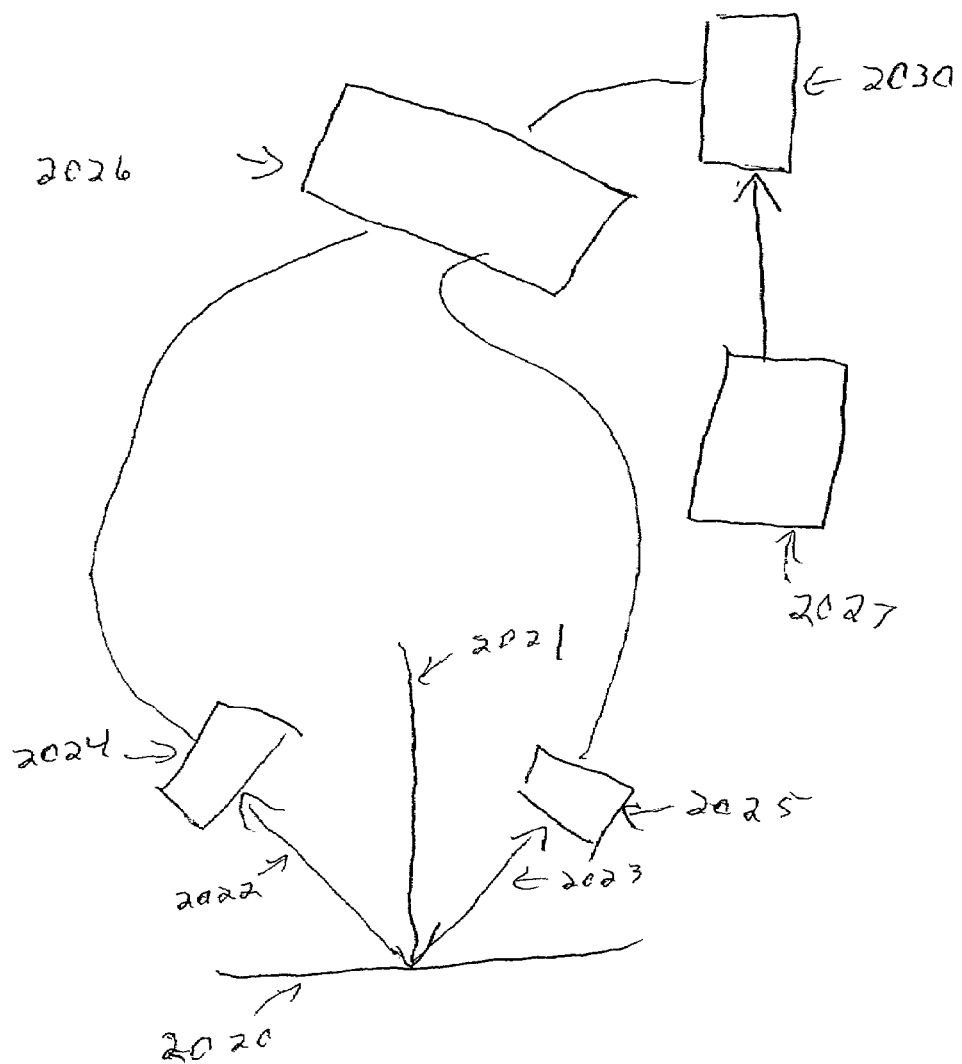
FIG. 20B illustrates an apparatus for use in a die to database mode

FIG. 20B illustrates an embodiment in which the output of two or more detectors is combined and compared with information derived from a design database (sometimes referred to as die to database mode). As shown in FIG. 20B, electrons from incident beam 2021 impinge upon substrate 2020, thereby producing secondary electrons 2022 and 2023. These electrons are detected by detectors 2024 and 2025. Information derived from these detectors may then be digitized in digitizer 2026. The information from the detectors may be combined either before digitization (while still in analog format), after digitization, or not combined at all. A design database, which was used in creating substrate 2020, may then be rendered into a rendered database 2027 to produce data in suitable format for comparison using computer 2030 with the digitized data output from digitizer 2024. The information from each detector can be compared individually to the rendered database, or the combined output of the detectors may be compared to the rendered database. A more detailed description of die to database inspection technology is contained in U.S. Pat. No. 4,926,487, which is hereby incorporated by reference.

Other Variations

For any of the methods described above, it may be advantageous, depending on the situation, either to digitize the data before processing it (to gain flexibility) or to process the raw data from the sensors in analog form (to gain speed or other advantages). For example, if the system contains two detectors mounted on opposite sides of the substrate, then the system could either add the two signals in analog form to simulate the signal from a detector placed above the substrate, or subtract the two signals in analog form to enhance a shadowing effect.

In other cases, it would be advantageous to filter out either the secondary electrons or the backscattered electrons before they reach a detector. Backscattered electrons tend to carry more information about the materials on the surface. Secondary electrons, which have energies up to 50 eV, tend to carry more topographic information and information about charging on the surface.

In still other cases, it would be advantageous to insert a dispersive element such as a magnetic separator, an energy-dispersive prism, or a Wien filter, which would cause low-energy electrons to strike one detector and high-energy electrons to strike another.

While many embodiments of this invention are described as using two detectors, those methods could readily be extended to use three or more detectors in an analogous fashion.

While many of the preceding examples discuss processing gray scale values of pixels, it is possible to additionally or alternatively process other information derived from the detector signals. Examples of such other information include the magnitude of the gradient of the gray scale pixels, the phase or direction of the gradient, and/or the curvature of the gradient contour. A more thorough discussion of the processing of such variables is found in U.S. Pat. No. 5,717,204, which is hereby incorporated by reference.

Although the invention has been described in relation to various implementations, together with modifications, variations, and extensions thereof, other implementations, modifications, variations and extensions are within the scope of the invention. Other embodiments may be apparent to those skilled in the art from consideration of the specification and invention disclosed herein. The invention is therefore not limited by the description contained herein or by the drawings, but only by the claims and their equivalents.

We claim the following inventions:

1. A method of inspecting and/or characterizing a substrate, comprising:

obtaining a first dataset ($D_{A1}$), wherein said first dataset includes data derived from an image collected by a first detector of a first region of said substrate;

obtaining a second dataset ($D_{B1}$), wherein said second dataset includes data derived from an image collected by a second detector of at least a portion of said first region of said substrate;

obtaining a third dataset ($D_{A2}$), wherein said third dataset includes data derived from an image collected by said first detector from a second region of said substrate, wherein said second region of said substrate is expected to be substantially identical to said first region;

obtaining a fourth dataset ($D_{B2}$), wherein said fourth dataset includes data derived from an image collected by said second detector of at least a portion of said second region of said substrate; and processing information derived from said first, second, third and fourth datasets to detect a defect in at least one of said first or second regions using a generalized equation of a form $$A = (P(BD_{A1} + CD_{B1})^M / (SD_{A1} + TD_{B1})^Q + (ED_{A2} + FD_{B2})^N / (UD_{A2} + VD_{B2})^R)^k,$$

where values of B, C, E, F, M, K, P, Q, R, S, T, U, V, and N represent constants and/or functions of other variables, wherein said information processing further includes calculating a first function representing comparison between said first and third datasets and calculating a second function representing comparison between said second and fourth data sets; and classifying the detected defect using output values of the first and second functions.

2. The method of claim 1 wherein the step of processing information comprises:

calculating the difference signal for each pixel with said first detector, calculating the difference signal for each pixel with said second detector, performing a math ematical operation on the two difference signals, and comparing the result of said operation with a threshold.

3. The method of claim 1, wherein said comparison is an image substraction.

4. The method of claim 1, wherein defects whose output values of the first and second functions cluster together are classified as a same defect type.

5. The method of claim 4, wherein at least two portions of said substrate are exposed to charged particles, and wherein said detectors are used to detect charged particles emitted from said portions, and wherein data from said detectors is used to determine whether potential defects exist within said portions.

* * * * *